(12) United States Patent
Schweinsberg

(10) Patent No.: US 9,161,898 B2
(45) Date of Patent: *Oct. 20, 2015

(54) COMPOSITIONS FOR COLOURING KERATIN FIBRES

(71) Applicant: Henkel AG & Co. KGaA, Düsseldorf (DE)

(72) Inventor: Matthias Schweinsberg, Hamburg (DE)

(73) Assignee: HENKEL AG & CO. KGAA, Duesseldorf (DE)

( * ) Notice: Subject to any disclaimer, the term of this patent is extended or adjusted under 35 U.S.C. 154(b) by 0 days.

This patent is subject to a terminal disclaimer.

(21) Appl. No.: 14/303,412

(22) Filed: Jun. 12, 2014

(65) Prior Publication Data

US 2014/0290690 A1 Oct. 2, 2014

Related U.S. Application Data

(63) Continuation of application No. PCT/EP2012/071819, filed on Nov. 5, 2012.

(30) Foreign Application Priority Data

Dec. 13, 2011 (DE) .......................... 10 2011 088 397

(51) Int. Cl.
*A61Q 5/10* (2006.01)
*A61K 8/73* (2006.01)
*A61Q 5/00* (2006.01)

(52) U.S. Cl.
CPC . *A61K 8/732* (2013.01); *A61Q 5/10* (2013.01); *A61Q 5/004* (2013.01)

(58) Field of Classification Search
CPC ........... A61Q 5/10; A61Q 5/004; A61K 8/22; A61K 8/732
USPC .................................... 8/405, 406, 408, 552
See application file for complete search history.

(56) References Cited

U.S. PATENT DOCUMENTS

| 8,603,447 | B2* | 12/2013 | Mueller et al. ............. 424/70.11 |
| 8,609,078 | B2* | 12/2013 | Schweinsberg et al. ... 424/70.13 |
| 8,790,628 | B2* | 7/2014 | Schweinsberg et al. ... 424/70.13 |
| 2004/0078905 | A1* | 4/2004 | Terranova et al. ................ 8/405 |
| 2004/0234486 | A1* | 11/2004 | Hashimoto ................ 424/70.16 |
| 2012/0207695 | A1* | 8/2012 | Schweinsberg et al. ... 424/70.13 |

FOREIGN PATENT DOCUMENTS

| EP | 0761200 A2 | 3/1997 |
| EP | 998908 A2 | 5/2000 |
| EP | 1568351 A1 | 8/2005 |
| FR | 2944967 A1 | 11/2010 |
| JP | 2010215599 A | 9/2010 |
| WO | 9801109 A1 | 1/1998 |
| WO | 2005034893 A1 | 4/2005 |
| WO | 2005082321 A1 | 9/2005 |
| WO | 2012084904 A1 | 6/2012 |
| WO | 2013023855 A2 | 2/2013 |

OTHER PUBLICATIONS

Saowakon Wattanachant et al: "Effect of crosslinking reagents and hydroxypropylation levels on dual-modified sago starch properties". Food Chemistry, vol. 80. Issue No. 4, Apr. 1, 2003. pages 463-471; abstract only.
Singh et al: "Factors influencing the physico-chemical, morphological, thermal and rheological properties of some chemically modified starches for food applications-A review", Food Hydrocolloids, vol. 21. Issue 1., Jan. 1, 2007, pp. 1-22.; abstract only.
Database WPI, Week 201067, Thomson Scientific, London, GB; AN 2010-M48909, XP002728050, 2004.

* cited by examiner

*Primary Examiner* — Eisa Elhilo
(74) *Attorney, Agent, or Firm* — Steven L. Nichols; Van Cott, Bagley, Cornwall & McCarthy P.C.

(57) ABSTRACT

The present specification provides for a cosmetic agent for coloring keratinic fibers. The agent includes, in a cosmetic carrier at least one color imparting compound and at least one modified starch. The modified starch is modified by propylene oxide, has an average molecular weight between 50 and 2500 kiloDaltons (kDa), and has a propylene oxide content between 0.1 and 20.0 wt % based on the weight of the modified starch.

19 Claims, No Drawings

COMPOSITIONS FOR COLOURING KERATIN FIBRES

RELATED DOCUMENTS

The present application is a U.S. continuation patent application under 35 U.S.C. 111(a) and claims the right of priority under 35 U.S.C. 365 to international patent Application No. PCT/EP2012/071819, filed Nov. 5, 2012, entitled "Compositions for Colouring Kerating Fibres" which claims benefit of German application No.: 102011088397.5, filed Dec. 13, 2011, these applications are herein incorporated by reference in their entirety.

FIELD OF THE INVENTION

The present application relates to cosmetic agents for coloring keratinic fibers, including in a cosmetic carrier at least one color-imparting compound and at least one starch, modified by means of propylene oxide, that possesses an average molecular weight (weight-average) from 50 to 2500 kiloDaltons (kDa) and has a propylene oxide content from 0.1 to 20.0 weight percent (wt %) based on the weight of the starch modified by means of propylene oxide.

BACKGROUND OF THE INVENTION

There are a variety of coloring systems, depending on the coloring requirements, for applying cosmetic agents for coloring, in particular to keratinic fibers such as human hair.

For permanent, intense color results with corresponding fastness properties, so-called oxidizing coloring agents are used. Such coloring agents usually include oxidation dye precursors called "developer components" and "coupler components." The developer components, under the influence of oxidizing agents or atmospheric oxygen, form the actual dyes with one another or are coupled to one or more coupler components. Oxidizing coloring agents are notable for outstanding, long-lasting color results. For natural-looking colors, however, it is usually necessary to use a mixture of a larger number of oxidation dye precursors; in many cases, substantive dyes are also used for toning.

Primary aromatic amines having a further free or substituted hydroxy or amino group located in the para- or ortho-position, heterocyclic hydrazones, diaminopyrazole derivatives, and 2,4,5,6-tetraaminopyrimidine and derivatives thereof, may be used as developer components. M-phenylenediamine derivatives, naphthols, pyridine derivatives, resorcinol and resorcinol derivatives, pyrazolones, and m-aminophenols may be used as coupler components.

For temporary coloring, coloring or tinting agents that include so-called "substantive" dyes as a coloring component may be used. These are dye molecules that absorb directly onto the substrate and do not require an oxidative process in order to form the color. These color results are appreciably more sensitive to shampooing than the oxidative colors, so that an often undesired shift in tone, or even visible homogeneous "decoloring," then occurs very much more quickly.

Lastly, a further coloring method has attracted much attention. In this method, precursors of melanin, a natural hair dye, are applied onto the substrate, e.g. hair; these precursors then form bioanalogous dyes in the context of oxidative processes. When agents having 5,6-dihydroxyindoline are used, in particular repeatedly, it is possible to restore the natural hair color to people with graying hair. Coloring can occur using atmospheric oxygen as the only oxidizing agent, so that no further oxidizing agents need to be utilized. For persons originally having medium-blonde to brown hair, indoline can be used as the only dye precursor. For use on persons having originally red, and in particular a dark to black hair color, on the other hand, satisfactory results can often be achieved only with the concurrent use of further dye components, in particular special oxidation dye precursors.

Improving the coloring performance of coloring agents is a constant aspiration. European patent application EP A1 1 568 351 discloses the use of a composition, comprising a starch including pregelatinized amylose, to preserve artificial color on hair.

International patent application WO-A1-98/01109 relates to agents for cleaning or caring for hair, the agent including a pregelatinized crosslinked starch selected from a ($C_2$ to $C_6$) hydroxyalkyl starch and a ($C_2$ to $C_6$) acyl starch. These agents, and others, however, are still capable of improvement.

For example, the color intensity, or coloring strength, of the dyes used has the consequence that costly dyes may be used more economically. The color results obtained are furthermore intended to exhibit a high degree of color fastness with regard to, for example, perspiration, washing, light, or friction, and should be compatible with the use of other hair treatment agents, in particular in the context of hair care. Uniform coloring along the keratinic fibers likewise presents a challenge to a commercially successfully coloring agent for keratinic fibers. Keratinic fibers, in particular human hairs, are natural products that grow, and are thus inhomogeneous in terms of their structural nature along the fiber. For example, the keratinic material of the fiber along the length of the hair and at the ends of the hair has been exposed for a longer period of time to environmental influences than the regions of the fiber in the vicinity of the hair root. The fibers along the length of the hair and at the ends of the hair therefore exhibit greater changes in the originally grown fiber structure. Differences in fiber structure often result in inhomogeneous color uptake and in inhomogeneous wearing away of the color as a result of environmental influences. As a result, the color is perceived visually as inhomogeneous.

The object of the present specification was therefore to furnish a cosmetic composition that colors keratinic fibers and that produces improved coloring and does not exhibit the aforementioned disadvantages.

Furthermore, other desirable features and characteristics of the present invention will become apparent from the subsequent detailed description of the invention and the appended claims, taken in conjunction with the accompanying drawings and this background of the invention.

BRIEF SUMMARY OF THE INVENTION

The present specification describes a cosmetic agent for coloring keratinic fibers. The agent includes, in a cosmetic carrier at least one color-imparting compound and at least one modified starch. The modified starch is modified by propylene oxide, has an average molecular weight between 50 and 2500 kiloDaltons (kDa), and has a propylene oxide content from 0.1 to 20.0 weight percent (wt %) based on the weight of the modified starch.

The present specification describes a method for providing a color treatment to keratinic fibers. The method includes, applying at least one modified starch to keratinic fibers artificially colored with at least one color-imparting compound. The modified starch is modified by propylene oxide, has an average molecular weight between 50 and 2500 kiloDaltons (kDa), and has a propylene oxide content between 0.1 to 20.0 wt % based on the weight of the modified starch. The method also includes rinsing the at least one modified starch off the keratinic fibers after a contact time.

The present specification describes a method for using at least one modified starch to improve artificial color results of color-imparting compounds on hair. The method includes applying the at least one modified starch to hair. The at least one modified starch is modified by propylene oxide, has an average molecular weight between 50 and 2500 kiloDaltons (kDa), and has a propylene oxide content between 0.1 to 20.0 wt % based on the weight of the modified starch. The method also includes rinsing the modified starch from the hair.

DETAILED DESCRIPTION

The following detailed description of the invention is merely exemplary in nature and is not intended to limit the invention or the application and uses of the invention. Furthermore, there is no intention to be bound by any theory presented in the preceding background of the invention or the following detailed description of the invention.

The use of the starch modified by means of propylene oxide on previously colored keratinic fibers (in particular during the coloring operation) improves the color fastness of the color result, in particular the washing fastness of the color result. Repeated washing of the fiber does not result in inhomogeneous coloring due to inhomogeneous washing out of the color along the keratinic fiber from the root to the ends. The color also maintains a good balance.

As used in the present specification and in the appended claims, the term "keratinic fibers" refer to furs, wool, feathers, and in particular human hair.

A starch is a reserve carbohydrate that is stored by many plants in the form of starch grains (granules), usually 1 to 200 micrometers (μm) in size, in various parts of the plant, for example in tubers or roots, cereal seeds, fruits, and in the pith. A starch modified by means of propylene oxide that may be used according to the present specification is derived preferably from at least one starch from potatoes, corn, rice, peas, acorns, chestnuts, barley, wheat, bananas, sago, millet, sorghum, oats, barley, rye, beans, yams, arrowroot or cassava. Particularly pronounced effects according to the present specification are achieved with corresponding tapioca starch modified by means of propylene oxide, potato starch modified by means of propylene oxide, corn starch modified by means of propylene oxide, or mixtures thereof. It is very particularly preferred according to the present specification to use tapioca starch modified by means of propylene oxide as a corresponding starch modified by means of propylene oxide.

Starch belongs to the homoglycan family and is a polycondensation product of D-glucose. Starch is made up of three structurally different polymers of d-glucopyranose, namely amylose, amylopectin, and a so-called intermediate fraction. Higher plants include between 0 and 45 wt % amylose, based on dry substance.

The intermediate fraction, which is also referred to as "anomalous amylopectin," is structurally intermediate between amylose and amylopectin. The quantitative indications defined in the context of the present specification for amylopectin include the intermediate fraction.

It is preferred according to the present specification if the starch modified by means of propylene oxide possesses an amylose content of less than 25 wt %, in particular less than 20 wt %, based in each case on the weight of said starch, It has been found that a starch that includes 17 to 22 wt % amylose and 78 to 83 wt % amylopectin is particularly suitable for achieving the effect according to the present specification.

Amylose is made up of predominantly linear α-1,4-glycosidically linked d-glucose, $M_r$ 50,000 to 150,000. The resulting chains form double helices in the starch.

Amylopectin also includes, besides the α-1,4 links described for amylose, α-1,6 bonds (in a quantity from 4 to 6%) as branching points. The average spacing between the branching points is approximately 12 to 17 glucose units. The molar mass of $10^7$ to $7*10^8$ corresponds to approx. $10^5$ glucose units, making amylopectin one of the largest biopolymers. The aforesaid branching points are distributed over the molecule in such a way that a bundle structure, with relatively short side chains, develops. Each double helix is formed by two of these side chains. As a result of the many branching points, amylopectin is relatively easily soluble in water.

As used in the present specification and in the appended claims, a "starch modified by means of propylene oxide," "a modified starch," "a starch modified by propylene oxide" or similar terminology is understood according to the present specification to refer to a reaction product of a starch with propylene oxide. A reaction product of this kind comprises at least one structural unit of formula (I)

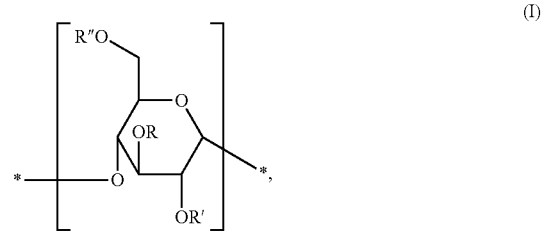

(I)

in which at least one residue R, R', or R" denotes a group of the formula

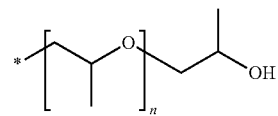

where n≥0, and at most two of the residues from among R, R', R" denote a hydrogen atom. In formulas of the present application, a bond identified with the * symbol corresponds to a free valence of the corresponding structural unit. The corresponding starches modified by means of propylene oxide are made available, for example, by reacting a natural starch with propylene oxide. Before modification by means of propylene oxide, the starch can have been exposed to a variety of physical or chemical processes, for example a heat treatment, shear, a thermal, acid-hydrolytic, oxidizing, or enzymatic cleavage, etc.

It is preferred according to the present specification if the starch modified by means of propylene oxide is not present in the agent according to the present specification in the form of individual starch grains (granules). For this purpose, the starch grains are disintegrated, for example by heat or shear, and the corresponding polysaccharide molecules are released from the network. The released polysaccharide molecules are modified by means of propylene oxide after or before release.

In the context of a preferred example, the starch modified by means of propylene oxide is gelatinized. When an aqueous suspension of starch is heated or compressed, a tangential swelling of the bodies is then observed at a critical temperature or pressure, with loss of birefringence, a change in X-ray structure, and an abrupt rise in the viscosity of the solution. This phenomenon is called "gelatinization."

The starches according to the present specification modified by means of propylene oxide are present in the agent according to the present specification in a molecular weight distribution. The molecular weight distribution was determined experimentally by gel filtration chromatography against dextran. An important feature of the present specification is the weight average of the average molecular weight of the starches, modified by means of propylene oxide, included in the agent according to the present specification. The aforesaid weight average is an average molecular weight that takes into account the total weight of the molecules of various molecular weights, and not simply the number of molecules. For statistical calculation of the weight average, firstly the "weight break" is defined by formula (1) as given below:

$$w_i = (N_i M_i)/[\Sigma(N_i M_i)] \quad \text{Formula (1).}$$

Formula (1) indicates the weight proportion, in the sample, of macromolecules that are made up of i segments (e.g. monomer modules) of mass $M_i$ and that occur $N_i$ times in the sample. The weight average of the molecular weight $M_w = \Sigma w_i M_i$ is thus given by formula (2) as given below:

$$M_w = [\Sigma(N_i M^2_i)]/[\Sigma(N_i M_i)] \quad \text{Formula (2).}$$

Particularly preferred agents according to the present specification include those aforesaid starches modified by means of propylene oxide which have an average molecular weight (weight-average) from 100 to 2000 kDa, in particular from 500 to 1800 kDa, very particularly preferably from 700 to 1000 kDa.

It is particularly preferred according to the present specification if the starch modified by means of propylene oxide, or modified starch, is uncrosslinked. Crosslinking of the starch modified by means of propylene oxide exists when the linear or branched polysaccharide macromolecules of the starch are linked covalently by means of a crosslinking agent, forming a three-dimensional, insoluble, and only swellable polymeric network. Natural starch is generally considered uncrosslinked and if crosslinking were desirable, requires artificial crosslinking by means of synthesis chemistry. Artificial crosslinking of this kind can be carried out using crosslinking agents, for example epichlorohydrin. Starches (modified by means of propylene oxide) that do not exhibit such crosslinking are uncrosslinked.

To achieve a lower molecular weight, for example, 700 to 900 kDa, the aforesaid starches are preferably exposed to a mechanical cleavage, enzymatic cleavage (in particular using alpha-amylase, beta-amylase, glucoamylase, or debranching enzymes), acid-hydrolytic cleavage (in particular using hydrochloric acid, sulfuric acid, or phosphoric acid), thermal cleavage, or a reaction with oxidizing agents (such as periodate, hypochlorite, chromic acid, permanganate, nitrogen dioxide, hydrogen peroxide, or organic percarboxylic acid, preferably with hydrogen peroxide). Kneaders, extruders, stator/rotor machines, and/or agitators are suitable for mechanical cleavage of the starch.

Oxidative cleavage using hydrogen peroxide is preferably suitable. For this purpose, for example, the starch modified by means of propylene oxide is added to water, heated to 50 to 70 degrees Celsius (° C.), hydrogen peroxide is added, and stirring occurs at 70 to 85° C. for 2 to 5 hours.

The propylene oxide content of the starch affects finetuning of the properties of the color obtained, and the stability of the cosmetic agents. The parameters can be further optimized if the aforesaid starch modified by means of propylene oxide has, based on the weight of the modified starch, a propylene oxide content from 2.0 to 12.0 wt %, particularly preferably a propylene oxide content from 3.0 to 10.0 wt %, very particularly preferably a propylene oxide content from 4.0 to 6.0 wt %. The propylene oxide content can be determined, for example, after carrying out a Hodges cleavage, using the method according to German Institute of Standardization standard "DIN EN 13268".

Those cosmetic agents in which the aforesaid starch modified by means of propylene oxide has, in a 43-wt % solution in water (i.e. in a 43-wt % aqueous solution), a preferred viscosity in the range from 150 to 1,500,000 millipascal-seconds (mPa·s) (as measured by a Brookfield viscometer, spindle 7 at 20° C. and at 20 rotations per minute (rpm)) are outstandingly suitable for purposes of the present specification. Outstandingly suitable propylene-oxide-modified polysaccharides have viscosities from 3000 to 200,000 mPa·s, in particular from 10,000 to 100,000 mPa·s, very particularly preferably from 40,000 to 70,000 mPa·s (measured in each case under the conditions recited above).

The color-imparting compounds for purposes of the present specification are preferably selected from 1) at least one oxidation dye precursor of the developer component type and optionally additionally at least one coupler component; 2) at least one substantive dye; and/or 3) from at least one precursor of bioanalogous dyes.

Particularly preferred color-imparting compounds are selected from at least one oxidation dye precursor of the developer component type and optionally at least one coupler component. Preferred representatives of the color-imparting compounds of (1), (2), and (3) (see above) are defined in the second subject of the present specification below.

The cosmetic use of the present specification is improved as said starch modified by means of propylene oxide is incorporated into a cosmetic carrier. The cosmetic agents recited below for coloring keratinic fibers, of the second subject of the present specification, are therefore preferred for use.

A second subject of the present specification is consequently a cosmetic agent for coloring keratinic fibers, in particular human hair, including in a cosmetic carrier at least one color-imparting compound and at least one modified starch. The modified starch is 1) modified by means of propylene oxide; 2) possesses an average molecular weight (weight-average) from 50 to 2500 kDa; and 3) has a propylene oxide content from 0.1 to 20.0 wt % (based on the weight of the starch modified by means of propylene oxide).

Preferred cosmetic carriers are aqueous cosmetic carriers, alcoholic cosmetic carriers, or aqueous alcoholic cosmetic carriers. For purposes of coloring keratinic fibers, such carriers are for example lotions, water-in-oil emulsions, oil-in-water emulsions, creams, gels, foams, or other preparations that are suitable for use on the hair. As used in the present specification and in the appended claims, an "aqueous alcoholic" carrier refers to aqueous compositions including 3.0 to 70.0 wt % of an organic solvent, in particular of a $C_1$ to $C_7$ alcohol (preferably ethanol, isopropanol, glycerol, benzyl alcohol, ethyl diglycol, 1,2-propylene glycol or 1,3-propylene glycol, methoxybutanol). All water-soluble organic solvents are preferred in this context.

The color-imparting compounds for purposes of the present specification are preferably selected from 1) at least one oxidation dye precursor of the developer component type and, optionally additionally at least one coupler component; 2) at least one substantive dye; and/or 3) at least one precursor of bioanalogous dyes.

It is preferred according to the present specification to use, as a developer component, a p-phenylenediamine derivative or a physiologically acceptable salt thereof. Particularly preferred are p-phenylenediamine derivatives of formula (E1).

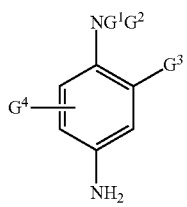

(E1)

In formula (E1):
- $G^1$ denotes a hydrogen atom, a ($C_1$ to $C_4$) alkyl residue, a ($C_1$ to $C_4$) monohydroxyalkyl residue, a ($C_2$ to $C_4$) polyhydroxyalkyl residue, a ($C_1$ to $C_4$) alkoxy-($C_1$ to $C_4$) alkyl residue, a 4'-aminophenyl residue, or a ($C_1$ to $C_4$) alkyl residue that is substituted with a nitrogen-containing group, with a phenyl residue, or with a 4'-aminophenyl residue;
- $G^2$ denotes a hydrogen atom, a ($C_1$ to $C_4$) alkyl residue, ($C_1$ to $C_4$) monohydroxyalkyl residue, a ($C_2$ to $C_4$) polyhydroxyalkyl residue, a ($C_1$ to $C_4$) alkoxy-($C_1$ to $C_4$) alkyl residue or a ($C_1$ to $C_4$) alkyl residue that is substituted with a nitrogen-containing group;
- $G^3$ denotes a hydrogen atom, a halogen atom such as a chlorine, bromine, iodine, or fluorine atom, a ($C_1$ to $C_4$) alkyl residue, a ($C_1$ to $C_4$) monohydroxyalkyl residue, a ($C_2$ to $C_4$) polyhydroxyalkyl residue, a ($C_1$ to $C_4$) hydroxyalkoxy residue, a ($C_1$ to $C_4$) acetylaminoalkoxy residue, a mesylamino-$C_1$ to $C_4$ alkoxy residue, or a ($C_1$ to $C_4$) carbamoylaminoalkoxy residue;
- $G^4$ denotes a hydrogen atom, a halogen atom, a ($C_1$ to $C_4$) alkyl residue, or a ($C_1$ to $C_4$) alkoxy-($C_1$ to $C_4$) alkyl residue; or
- if $G^3$ are $G^4$ are in the ortho-position with respect to one another, they can together form a bridging α,ω-alkylenedioxo group, for example an ethylenedioxy group.

Particularly preferred p-phenylenediamines of formula (E1)) are selected from one or more compounds of the group that is constituted from p-phenylenediamine, p-toluylenediamine, 2-chloro-p-phenylenediamine, 2,3-dimethyl-p-phenylenediamine, 2,6-dimethyl-p-phenylenediamine, 2,6-diethyl-p-phenylenediamine, 2,5-dimethyl-p-phenylenediamine, N,N-dimethyl-p-phenylenediamine, N,N-diethyl-p-phenylenediamine, N,N-dipropyl-p-phenylenediamine, 4-amino-3-methyl-(N,N-diethyl)aniline, N,N-bis-(β-hydroxyethyl)-p-phenylenediamine, 4-N,N-bis-hydroxyethyl)amino-2-methylaniline, 4-N,N-bis-(β-hydroxyethyl)amino-2-chloroaniline, 2-(β-hydroxyethyl)-p-phenylenediamine, 2-(α,β-dihydroxyethyl)-p-phenylenediamine, 2-fluoro-p-phenylenediamine, 2-isopropyl-p-phenylenediamine, N-(β-hydroxypropyl)-p-phenylenediamine, 2-hydroxymethyl-p-phenylenediamine, N,N-dimethyl-3-methyl-p-phenylenediamine, N,N-(ethyl,β-hydroxyethyl)-p-phenylenediamine, N-(β,γ-dihydroxypropyl)-p-phenylenediamine, N-(4'-aminophenyl)-p-phenylenediamine, N-phenyl-p-phenylenediamine, 2-(β-hydroxyethyloxy)-p-phenylenediamine, 2-methoxymethyl-p-phenylenediamine, 2-(β-acetylaminoethyloxy)-p-phenylenediamine, N-(β-methoxyethyl)-p-phenylenediamine, N-(4-amino-3-methylphenyl)-N-[3-(1H-imidazol-1-yl)propyl]amine, and 5,8-diaminobenzo-1,4-dioxane, as well as physiologically acceptable salts thereof.

p-Phenylenediamine derivatives of formula (E1)) that are very particularly preferred according to the present specification are selected from at least one compound of the group p-phenylenediamine, p-toluylenediamine, 2-(β-hydroxyethyl)-p-phenylenediamine, 2-(α,β-dihydroxyethyl)-p-phenylenediamine, N,N-bis-(β-hydroxyethyl)-p-phenylenediamine, 2-methoxymethyl-p-phenylenediamine, N-(4-amino-3-methylphenyl)-N-[3-(1H-imidazol-1-yl)propyl]amine,
and physiologically acceptable salts of said compounds.

It may furthermore be preferred according to the present specificastion to employ, as developer components, compounds that include at least two aromatic nuclei that are substituted with amino and/or hydroxyl groups.

Among the binuclear developer components that can be used in the coloring compositions in accordance with the present specification may be cited, in particular, those compounds which correspond to formula (E2) below, as well as physiologically acceptable salts thereof.

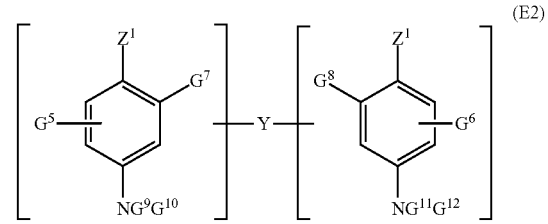

(E2)

In Formula (E2):
- $Z^1$ and $Z^2$ mutually independently denote a hydroxyl residue or $NH_2$ residue that is optionally substituted with a ($C_1$ to $C_4$) alkyl residue, with a ($C_1$ to $C_4$) hydroxyalkyl residue, and/or with a bridge Y, or that optionally is part of a bridging ring system;
- the bridge Y denotes an alkylene group having 1 to 14 carbon atoms, for example a linear or branched alkylene chain or an alkylene ring, which can be interrupted or terminated by one or more nitrogen-containing groups and/or by one or more heteroatoms such as oxygen, sulfur, or nitrogen atoms, and possibly can be substituted with one or more hydroxyl or ($C_1$ to $C_8$) alkoxy residues, or a direct bond;
- $G^5$ and $G^6$ mutually independently denote a hydrogen atom or halogen atom, a ($C_1$ to $C_4$) alkyl residue, a ($C_1$ to $C_4$) monohydroxyalkyl residue, a ($C_2$ to $C_4$) polyhydroxyalkyl residue, a ($C_1$ to $C_4$) aminoalkyl residue, or a direct bond to the bridge Y,
- $G^7$, $G^8$, $G^9$, $G^{10}$, $G^{11}$ and $G^{12}$ mutually independently denote a hydrogen atom, a direct bond to the bridge Y, or a ($C_1$ to $C_4$) alkyl residue.

In Formula (E2) the compounds include only one bridge Y per molecule. The substituents used in formula (E2) are defined according to the present specification by analogy with the statements made above.

Preferred binuclear developer components of formula (E2) are selected in particular from at least one of the following compounds: N,N'-bis-(β-hydroxyethyl)-N,N'-bis-(4'-aminophenyl)-1,3-diaminopropan-2-ol, N,N'-bis-(β-hydroxyethyl)-N,N'-bis-(4'-aminophenyl)ethylenediamine, N,N'-bis-(4-aminophenyl)tetramethylenediamine, N,N'-bis-(β-hydroxyethyl)-N,N'-bis-(4-aminophenyl) tetramethylenediamine, N,N'-bis-(4'-(methylamino)phenyl) tetramethylenediamine, N,N'-diethyl-N,N'-bis-(4'-amino-3'- methylphenyl)ethylenediamine, bis-(2-hydroxy-5-aminophenyl)methane, N,N'-bis-(4'-aminophenyl)-1,4-diazacycloheptane, N,N'-bis-(2-hydroxy-5-aminobenzyl)piperazine, N-(4'-aminophenyl)-p-phenylenediamine, and 1,10-bis-(2',5'-diaminophenyl)-1,4,7,10-tetraoxadecane, and physiologically acceptable salts thereof.

Very particularly preferred binuclear developer components of formula (E2) are selected from among N,N'-bis-(β-hydroxyethyl)-N,N'-bis-(4-aminophenyl)-1,3-diaminopropan-2-ol, bis-(2-hydroxy-5-aminophenyl)methane, 1,3-bis-(2-hydroxy-5-aminophenyl)methane, N,N'-bis-(4-aminophenyl)-1,4-diazacycloheptane, and 1,10-bis-(2,5-diaminophenyl)-1,4,7,10-tetraoxadecane, or a physiologically acceptable salt of said compounds.

It is furthermore preferred according to the present specification to use as a developer component at least one p-aminophenol derivative or a physiologically acceptable salt. p-Aminophenol derivatives of formula (E3) are particularly preferred.

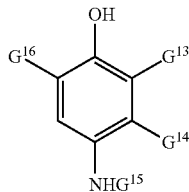

(E3)

In formula (E3), It is furthermore preferred according to the present specification to use as a developer component at least one p-aminophenol derivative or a physiologically acceptable salt. In formula (E3):

$G^{13}$ denotes a hydrogen atom, a halogen atom, a ($C_1$ to $C_4$) alkyl residue, a ($C_1$ to $C_4$) monohydroxyalkyl residue, a ($C_2$ to $C_4$) polyhydroxyalkyl residue, a ($C_1$ to $C_4$) alkoxy-($C_1$ to $C_4$) alkyl residue, a ($C_1$ to $C_4$) aminoalkyl residue, a hydroxy-($C_1$ to $C_4$) alkylamino residue, a ($C_1$ to $C_4$) hydroxyalkoxy residue, a ($C_1$ to $C_4$ hydroxyalkyl-($C_1$ to $C_4$) aminoalkyl residue, or a (di-[($C_1$ to $C_4$) alkyl] amino)-($C_1$ to $C_4$) alkyl residue, and $G^{14}$ denotes a hydrogen atom or halogen atom, a ($C_1$ to $C_4$) alkyl residue, a ($C_1$ to $C_4$) monohydroxyalkyl residue, a ($C_2$ to $C_4$) polyhydroxyalkyl residue, a ($C_1$ to $C_4$) alkoxy-($C_1$ to $C_4$) alkyl residue, a ($C_1$ to $C_4$) aminoalkyl residue, or a ($C_1$ to $C_4$) cyanoalkyl residue, $G^{15}$ denotes hydrogen, a ($C_1$ to $C_4$) alkyl residue, a ($C_1$ to $C_4$) monohydroxyalkyl residue, a ($C_2$ to $C_4$) polyhydroxyalkyl residue, a phenyl residue, or a benzyl residue, and $G^{16}$ denotes hydrogen or a halogen atom.

The substituents used in formula (E3) are defined according to the present specification by analogy with the statements above.

Preferred p-aminophenols of formula (E3) are, in particular, p-aminophenol, N-methyl-p-aminophenol, 4-amino-3-methylphenol, 4-amino-3-fluorophenol, 2-hydroxymethylamino-4-aminophenol, 4-amino-3-hydroxymethylphenol, 4-amino-2-(β-hydroxyethoxy)phenol, 4-amino-2-methylphenol, 4-amino-2-hydroxymethylphenol, 4-amino-2-methoxymethylphenol, 4-amino-2-aminomethylphenol, 4-amino-2-(β-hydroxyethylaminomethyl)phenol, 4-amino-2-(α,β-dihydroxyethyl)phenol, 4-amino-2-fluorophenol, 4-amino-2-chlorophenol, 4-amino-2,6-dichlorophenol, 4-amino-2-(diethylaminomethyl)phenol, and physiologically acceptable salts thereof.

Very particularly preferred compounds of formula (E3) are p-aminophenol, 4-amino-3-methylphenol, 4-amino-2-aminomethylphenol, 4-amino-2-(α,β-dihydroxyethyl)phenol, and 4-amino-2-(diethylaminomethyl)phenol.

The developer component can furthermore be selected from o-aminophenol and derivatives thereof such as, for example, 2-amino-4-methylphenol, 2-amino-5-methylphenol, or 2-amino-4-chlorophenol.

The developer component can moreover be selected preferably from heterocyclic developer components, for example from pyrimidine derivatives, pyrazole derivatives or physiologically acceptable salts thereof.

Preferred pyrimidine derivatives are selected according to the present specification from compounds according to formula (E4) and physiologically acceptable salts thereof.

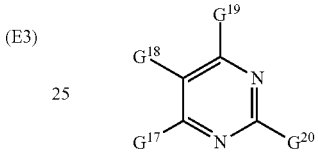

(E4)

In formula (E4):

$G^{17}$, $G^{18}$, and $G^{19}$ mutually independently denote a hydrogen atom, a hydroxy group, a ($C_1$ to $C_4$) alkoxy group, or an amino group; and $G^{20}$ denotes a hydroxy group or an —$NG^{21}G^{22}$ group in which $G^{21}$ and $G^{22}$ mutually independently denote a hydrogen atom, a ($C_1$ to $C_4$) alkyl group, a ($C_1$ to $C_4$) monohydroxyalkyl group.

In formula (E4), a maximum of two of the groups from among $G^{17}$, $G^{18}$, $G^{19}$, and $G^{20}$ signify a hydroxy group, and at most two of the residues $G^{17}$, $G^{18}$, and $G^{19}$ denote a hydrogen atom. It is in turn preferred if, in accordance with formula (E4), at least two groups from among $G^{17}$, $G^{18}$, $G^{19}$, and $G^{20}$ denote an —$NG^{21}G^{22}$ group, and at most two groups from among $G^{17}$, $G^{18}$, $G^{19}$ and $G^{20}$ denote a hydroxy group.

Particularly preferred pyrimidine derivatives are, in particular, the compounds 2,4,5,6-tetraaminopyrimidine, 4-hydroxy-2,5,6-triaminopyrimidine, 2-hydroxy-4,5,6-triaminopyrimidine, 2-dimethylamino-4,5,6-triaminopyrimidine, 2,4-dihydroxy-5,6-diaminopyrimidine, and 2,5,6-triaminopyrimidine.

Preferred pyrazole derivatives are selected according to the present specification from compounds according to formula (E5),

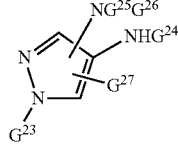

(E5)

In formula (E5):

$G^{23}$, $G^{24}$, $G^{25}$ mutually independently denote a hydrogen atom, a ($C_1$ to $C_4$) alkyl group, a ($C_1$ to $C_4$) monohydroxyalkyl group, a ($C_2$ to $C_4$) polyhydroxyalkyl group, an optionally substituted aryl group, or an optionally substituted aryl-($C_1$ to $C_4$) alkyl group, with the provision that if $G^{25}$ denotes a hydrogen atom, $G^{27}$ can additionally denote not only the aforesaid groups but additionally an —$NH_2$ group;

$G^{26}$ denotes a hydrogen atom, a ($C_1$ to $C_4$) alkyl group, a ($C_1$ to $C_4$) monohydroxyalkyl group, or a ($C_2$ to $C_4$) polyhydroxyalkyl group; and $G^{27}$ denotes a hydrogen atom, an optionally substituted aryl group, a ($C_1$ to $C_4$) alkyl group, or a ($C_1$ to $C_4$) monohydroxyalkyl group, in particular a hydrogen atom or a methyl group.

In formula (E5) the —$NG^{25}G^{26}$ residue preferably binds to the –5 position on the pyrazole cycle, and the $G^{27}$ residue to the –3 position.

Particularly preferred pyrazole derivatives are in particular the compounds selected from among 4,5-diamino-1-methylpyrazole, 4,5-diamino-1-(β-hydroxyethyl)pyrazole, 3,4-diaminopyrazole, 4,5-diamino-1-(4'-chlorobenzyl)pyrazole, 4,5-diamino-1,3-dimethylpyrazole, 4,5-diamino-3-methyl-1-phenylpyrazole, 4,5-diamino-1-methyl-3-phenylpyrazole, 4-amino-1,3-dimethyl-5-hydrazinopyrazole, 1-benzyl-4,5-diamino-3-methylpyrazole, 4,5-diamino-3-tert.-butyl-1-methylpyrazole, 4,5-diamino-1-tert.-butyl-3-methylpyrazole, 4,5-diamino-1-(β-hydroxyethyl)-3-methylpyrazole, 4,5-diamino-1-ethyl-3-methylpyrazole, 4,5-diamino-1-ethyl-3-(4'-methoxyphenyl)pyrazole, 4,5-diamino-1-ethyl-3-hydroxymethylpyrazole, 4,5-diamino-3-hydroxymethyl-1-methylpyrazole, 4,5-diamino-3-hydroxymethyl-1-isopropylpyrazole, 4,5-diamino-3-methyl-1-isopropylpyrazole, 4-amino-5-(β-aminoethyl)amino-1,3-dimethylpyrazole, and physiologically acceptable salts thereof.

Examples of the residues recited as substituents of the compounds of formulas (E1) to (E6) will be listed below: examples of ($C_1$ to $C_4$) alkyl residues are the groups —$CH_3$, —$CH_2CH_3$, —$CH_2CH_2CH_3$, —$CH(CH_3)_2$, —$CH_2CH_2CH_2CH_3$, —$CH_2CH(CH_3)_2$, —$CH(CH_3)CH_2CH_3$, —$C(CH_3)_3$. Examples according to the present specification of ($C_1$ to $C_4$) alkoxy residues are —$OCH_3$, —$OCH_2CH_3$, —$OCH_2CH_2CH_3$, —$OCH(CH_3)_2$, —$OCH_2CH_2CH_2CH_3$, —$OCH_2CH(CH_3)_2$, —$OCH(CH_3)CH_2CH_3$, —$OC(CH_3)_3$, in particular a methoxy or ethoxy group.

In addition, preferred examples of a ($C_1$ to $C_4$) monohydroxyalkyl group are —$CH_2OH$, —$CH_2CH_2OH$, —$CH_2CH_2CH_2OH$, —$CHCH(OH)CH_3$, —$CH_2CH_2CH_2CH_2OH$, the —$CH_2CH_2OH$ group being preferred. A particularly preferred example of a ($C_2$ to $C_4$) polyhydroxyalkyl group is the 1,2-dihydroxyethyl group. Examples of halogen atoms are F, Cl, or Br atoms; Cl atoms are very particularly preferred examples. Examples of nitrogen-containing groups are, in particular, —$NH_2$, ($C_1$ to $C_4$) monoalkylamino groups, ($C_1$ to $C_4$) dialkylamino groups, ($C_1$ to $C_4$) trialkylammonium groups, ($C_1$ to $C_4$) monohydroxyalkylamino groups, imidazolinium, and —$NH_3^+$. Examples of ($C_1$ to $C_4$) monoalkylamino groups are —$NHCH_3$, —$NHCH_2CH_3$, —$NHCH_2CH_2CH_3$, —$NHCH(CH_3)_2$.

Examples of a ($C_1$ to $C_4$) dialkylamino group are —$N(CH_3)_2$, —$N(CH_2CH_3)_2$. Examples of ($C_1$ to $C_4$) trialkylammonium groups are —$N^+(CH_3)_3$, —$N^+(CH_3)_2(CH_2CH_3)$, —$N^+(CH_3)(CH_2CH_3)_2$.

Examples of ($C_1$ to $C_4$) hydroxyalkylamino residues are —$NH$—$CH_2CH_2OH$ and —$NH$—$CH_2CH_2CH_2OH$. Examples of ($C_1$ to $C_4$) alkoxy-($C_1$ to $C_4$) alkyl groups are the —$CH_2CH_2$—O—$CH_3$, —$CH_2CH_2CH_2$—O—$CH_3$, —$CH_2CH_2$—O—$CH_2CH_3$, —$CH_2CH_2CH_2$—O—$CH_2CH_3$, —$CH_2CH_2$—O—$CH(CH_3)$, —$CH_2CH_2CH_2$—O—$CH(CH_3)$ groups.

Examples of hydroxy-($C_1$ to $C_4$) alkoxy residues are —O—$CH_2OH$, —O—$CH_2CH_2OH$, —O—$CH_2CH_2CH_2OH$, —O—$CHCH(OH)CH_3$, —O—$CH_2CH_2CH_2CH_2OH$. Examples of ($C_1$ to $C_4$) acetylaminoalkoxy residues are —O—$CH_2NHC(O)CH_3$, —O—$CH_2CH_2NHC(O)CH_3$, —O—$CH_2CH_2CH_2NHC(O)CH_3$, —O—$CH_2CH(NHC(O)CH_3)CH_3$, —O—$CH_2CH_2CH_2CH_2NHC(O)CH_3$. Examples of ($C_1$ to $C_4$) carbamoylaminoalkoxy residues are —O—$CH_2CH_2$—NH—C(O)—$NH_2$, —O—$CH_2CH_2CH_2$—NH—C(O)—$NH_2$, —O—$CH_2CH_2CH_2CH_2$—NH—C(O)—$NH_2$.

Examples of ($C_1$ to $C_4$) aminoalkyl residues are —$CH_2NH_2$, —$CH_2CH_2NH_2$, —$CH_2CH_2CH_2NH_2$, —$CH_2CH(NH_2)CH_3$, —$CH_2CH_2CH_2CH_2NH_2$.

Examples of ($C_1$ to $C_4$) cyanoalkyl residues are —$CH_2CN$, —$CH_2CH_2CN$, —$CH_2CH_2CH_2CN$.

Examples of ($C_1$ to $C_4$) hydroxyalkylamino-($C_1$ to $C_4$) alkyl residues are —$CH_2CH_2NH$—$CH_2CH_2OH$, —$CH_2CH_2CH_2NH$—$CH_2CH_2OH$, —$CH_2CH_2NH$—$CH_2CH_2CH_2OH$, —$CH_2CH_2CH_2NH$—$CH_2CH_2CH_2OH$.

Examples of di[($C_1$ to $C_4$) hydroxyalkyl]amino-($C_1$ to $C_4$) alkyl residues are —$CH_2CH_2N(CH_2CH_2OH)_2$, —$CH_2CH_2CH_2N(CH_2CH_2OH)_2$, —$CH_2CH_2N(CH_2CH_2CH_2OH)_2$, —$CH_2CH_2CH_2N(CH_2CH_2CH_2OH)_2$. An example of aryl groups is the phenyl group.

Examples of aryl-($C_1$ to $C_4$) alkyl groups are the benzyl group and the 2-phenylethyl group.

Coupler components for purposes of the present specification allow at least one chemical residue of the coupler to be substituted with the oxidized form of the developer component, in which context a covalent bond forms between the coupler component and developer component. Couplers are preferably cyclic compounds that carry on the cycle at least two groups selected from (i) optionally substituted amino groups, and/or (ii) hydroxyl groups. If the cyclic compound is a six-membered ring (preferably aromatic), the aforesaid groups are then located preferably in the ortho- or meta-position with respect to one another.

Coupler components according to the present specification are preferably selected from at least one component of one of the following classes:
  m-aminophenol and/or derivatives thereof,
  m-diaminobenzene and/or derivatives thereof,
  o-diaminobenzene and/or derivatives thereof,
  o-aminophenol derivatives, for example o-aminophenol,
  naphthalene derivatives having at least one hydroxy group,
  di- or trihydroxybenzene and/or derivatives thereof,
  pyridine derivatives,
  pyrimidine derivatives,
  monohydroxyindole derivatives and/or monoaminoindole derivatives,
  monohydroxyindoline derivatives and/or monoaminoindoline derivatives
  pyrazolone derivatives, for example 1-phenyl-3-methylpyrazol-5-one,
  morpholine derivatives, for example 6-hydroxybenzomorpholine or 6-aminobenzomorpholine,
  quinoxaline derivatives, for example 6-methyl-1,2,3,4-tetrahydroquinoxaline;
mixtures of two or more compounds from one or more of these classes are likewise preferred according to the present specification in the context of this example.

The m-aminophenols or derivatives thereof usable according to the present specification are preferably selected from at least one compound of formula (K1) and/or from at least one physiologically acceptable salt of a compound in accordance with formula (K1).

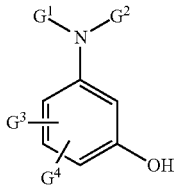

(K1)

In formula (K1):
$G^1$ and $G^2$ mutually independently denote a hydrogen atom, a ($C_1$ to $C_4$) alkyl group, a ($C_3$ to $C_6$) cycloalkyl group, a ($C_2$ to $C_4$) alkenyl group, a ($C_1$ to $C_4$) monohydroxyalkyl group, a ($C_2$ to $C_4$) polyhydroxyalkyl group, a ($C_2$ to $C_4$) perfluoracyl group, an aryl-($C_1$ to $C_6$) alkyl group, an amino-($C_1$ to $C_6$) alkyl group, a ($C_1$ to $C_6$) dialkylamino-($C_1$ to $C_6$) alkyl group, or a ($C_1$ to $C_6$) alkoxy-($C_1$ to $C_6$) alkyl group, wherein $G^1$ and $G^2$, together with the nitrogen atom, can form a five-, six, or seven-membered ring;
$G^3$ and $G^4$ mutually independently denote a hydrogen atom, a halogen atom, a ($C_1$ to $C_4$) alkyl group, a ($C_1$ to $C_4$) alkoxy group, a hydroxy group, a ($C_1$ to $C_4$) monohydroxyalkyl group, a ($C_2$ to $C_4$) polyhydroxyalkyl group, a hydroxy-($C_1$ to $C_4$) alkoxy group, a ($C_1$ to $C_6$) alkoxy-($C_2$ to $C_6$) alkoxy group, an aryl group, or a heteroaryl group.

Particularly preferred m-aminophenol coupler components are selected from at least one compound of the group that is constituted from m-aminophenol, 5-amino-2-methylphenol, N-cyclopentyl-3-aminophenol, 3-amino-2-chloro-6-methylphenol, 2-hydroxy-4-aminophenoxyethanol, 2,6-dimethyl-3-aminophenol, 3-trifluoroacetylamino-2-chloro-6-methylphenol, 5-amino-4-chloro-2-methylphenol, 5-amino-4-methoxy-2-methylphenol, 5-(2'-hydroxyethyl)amino-2-methylphenol, 3-(diethylamino)phenol, N-cyclopentyl-3-aminophenol, 1,3-dihydroxy-5-(methylamino)benzene, 3-ethylamino-4-methylphenol, 2,4-dichloro-3-aminophenol, and physiologically acceptable salts of all the compounds recited above.

The m-diaminobenzenes or derivatives thereof usable according to the present specification are preferably selected from at least one compound of formula (K2) and/or from at least one physiologically acceptable salt of a compound in accordance with formula (K2).

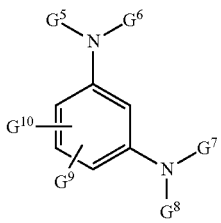

(K2)

In formula (K2):
$G^5$, $G^6$, $G^7$, and $G^8$ mutually independently denote a hydrogen atom, a ($C_1$ to $C_4$) alkyl group, a ($C_3$ to $C_6$) cycloalkyl group, a ($C_2$ to $C_4$) alkenyl group, a ($C_1$ to $C_4$) monohydroxyalkyl group, a ($C_2$ to $C_4$) polyhydroxyalkyl group, a ($C_1$ to $C_4$) alkoxy-($C_1$ to $C_4$) alkyl group, an aryl-($C_1$ to $C_4$) alkyl group, a heteroaryl-($C_1$ to $C_4$) alkyl group, a ($C_2$ to $C_4$) perfluoracyl group, or form, together with the nitrogen atom, a five- or six-membered heterocycle;
$G^9$ and $G^{10}$ mutually independently denote a hydrogen atom, a halogen atom, a ($C_1$ to $C_4$) alkyl group, an ω-(2,4-diaminophenyl)-($C_1$ to $C_4$) alkyl group, an ω-(2,4-diaminophenyloxy)-($C_1$ to $C_4$) alkoxy group, a ($C_1$ to $C_4$) alkoxy group, a hydroxy group, a ($C_1$ to $C_4$) alkoxy-($C_2$ to $C_4$) alkoxy group, an aryl group, a heteroaryl group, a ($C_1$ to $C_4$) monohydroxyalkyl group, a ($C_2$ to $C_4$) polyhydroxyalkyl group, a hydroxy-($C_1$ to $C_4$) alkoxy group.

Particularly preferred m-diaminobenzene coupler components are selected from at least one compound of the group that is constituted from m-phenylenediamine, 2-(2,4-diaminophenoxy)ethanol, 1,3-bis(2,4-diaminophenoxy)propane, 1-methoxy-2-amino-4-(2'-hydroxyethylamino)benzene, 1,3-bis(2,4-diaminophenyl)propane, 2,6-bis(2'-hydroxyethylamino)-1-methylbenzene, 2-({3-[(2-hydroxyethyl)amino]-4-methoxy-5-methylphenyl}amino)ethanol, 2-({3-[(2-hydroxyethyl)amino]-2-methoxy-5-methylphenyl}amino)ethanol, 2-({3-[(2-hydroxyethyl)amino]-4,5-dimethylphenyl}amino)ethanol, 2-[3-morpholin-4-ylphenyl)amino]ethanol, 3-amino-4-(2-methoxyethoxy)-5-methylphenylamine, 1-amino-3-bis-(2'-hydroxyethyl)aminobenzene, and physiologically acceptable salts of all the compounds recited above.

The o-diaminobenzenes or derivatives thereof usable according to the present specification are preferably selected from at least one compound of formula (K3) and/or from at least one physiologically acceptable salt of a compound in accordance with formula (K3).

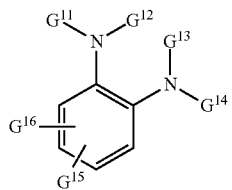

(K3)

In formula (K3):
$G^{11}$, $G^{12}$, $G^{13}$, and $G^{14}$ mutually independently denote a hydrogen atom, a ($C_1$ to $C_4$) alkyl group, a ($C_3$ to $C_6$) cycloalkyl group, a ($C_2$ to $C_4$) alkenyl group, a ($C_1$ to $C_4$) monohydroxyalkyl group, a ($C_2$ to $C_4$) polyhydroxyalkyl group, a ($C_1$ to $C_4$) alkoxy-($C_1$ to $C_4$) alkyl group, an aryl-($C_1$ to $C_4$) alkyl group, a heteroaryl-($C_1$ to $C_4$) alkyl group, a ($C_2$ to $C_4$) perfluoracyl group, or form, together with the nitrogen atom, a five- or six-membered heterocycle;
$G^{15}$ and $G^{16}$ mutually independently denote a hydrogen atom, a halogen atom, a carboxyl group, a ($C_1$ to $C_4$) alkyl group, a ($C_1$ to $C_4$) alkoxy group, a hydroxy group, a ($C_1$ to $C_4$) monohydroxyalkyl group, a ($C_2$ to $C_4$) polyhydroxyalkyl group, a hydroxy-($C_1$ to $C_4$) alkoxy group.

Particularly preferred o-diaminobenzene coupler components are selected from at least one compound of the group that is constituted from 3,4-diaminobenzoic acid and 2,3-diamino-1-methylbenzene, and physiologically acceptable salts of all the compounds recited above.

Preferred di- or trihydroxybenzenes and derivatives thereof are selected from at least one compound of the group that is constituted from resorcinol, resorcinol monomethyl ether, 2-methylresorcinol, 5-methylresorcinol, 2,5-dimethylresorcinol, 2-chlororesorcinol, 4-chlororesorcinol, pyrogallol, and 1,2,4-trihydroxybenzene.

The pyridine derivatives usable according to the present specification are preferably selected from at least one compound of formula (K4) and/or from at least one physiologically acceptable salt of a compound in accordance with formula (K4).

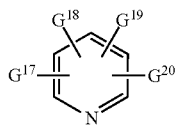

(K4)

In formula (K4):
$G^{17}$ and $G^{18}$ mutually independently denote a hydroxy group or an —$NG^{21}G^{22}$ group, in which $G^{21}$ and $G^{22}$ mutually independently denote a hydrogen atom, a ($C_1$ to $C_4$) alkyl group, a ($C_3$ to $C_6$) cycloalkyl group, a ($C_2$ to $C_4$) alkenyl group, an aryl group, a ($C_1$ to $C_4$) monohydroxyalkyl group, a ($C_2$ to $C_4$) polyhydroxyalkyl group, a ($C_1$ to $C_4$) alkoxy-($C_1$ to $C_4$) alkyl group, an aryl-($C_1$ to $C_4$) alkyl group, a heteroaryl-($C_1$ to $C_4$) alkyl group, $G^{19}$ and $G^{20}$ mutually independently denote a hydrogen atom, a halogen atom, a ($C_1$ to $C_4$) alkyl group, or a ($C_1$ to $C_4$) alkoxy group.

It is preferred if, in accordance with formula (K4), the $G^{17}$ and $G^{18}$ residues are in the ortho- or meta-position with respect to one another.

Particularly preferred pyridine derivatives are selected from at least one compound of the group that is constituted from 2,6-dihydroxypyridine, 2-amino-3-hydroxypyridine, 2-amino-5-chloro-3-hydroxypyridine, 3-amino-2-methylamino-6-methoxypyridine, 2,6-dihydroxy-3,4-dimethylpyridine, 2,6-dihydroxy-4-methylpyridine, 2,6-diaminopyridine, 2,3-diamino-6-methoxypyridine, 3,5-diamino-2,6-dimethoxypyridine, 3,4-diaminopyridine, 2-(2-methoxyethyl)amino-3-amino-6-methoxypyridine, 2-(4'-methoxyphenyl)amino-3-aminopyridine, and physiologically acceptable salts of the aforesaid compounds.

Preferred naphthalene derivatives having at least one hydroxy group are selected from at least one compound of the group that is constituted from 1-naphthol, 2-methyl-1-naphthol, 2-hydroxymethyl-1-naphthol, 2-hydroxyethyl-1-naphthol, 1,3-dihydroxynaphthalene, 1,5-dihydroxynaphthalene, 1,6-dihydroxynaphthalene, 1,7-dihydroxynaphthalene, 1,8-dihydroxynaphthalene, 2,7-dihydroxynaphthalene, and 2,3-dihydroxynaphthalene.

The indole derivatives usable according to the present specification are preferably selected from at least one compound of formula (K5) and/or from at least one physiologically acceptable salt of a compound in accordance with formula (K5).

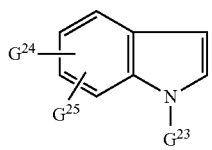

(K5)

In formula (K5):
$G^{23}$ denotes a hydrogen atom, a ($C_1$ to $C_4$) alkyl group, a ($C_3$ to $C_6$) cycloalkyl group, a ($C_2$ to $C_4$) alkenyl group, a ($C_1$ to $C_4$) monohydroxyalkyl group, a ($C_2$ to $C_4$) polyhydroxyalkyl group, an aryl-($C_1$ to $C_4$) alkyl group, $G^{24}$ denotes a hydroxy group or an —$NG^{26}G^{27}$ group, in which $G^{26}$ and $G^{27}$ mutually independently denote a hydrogen atom, a ($C_1$ to $C_4$) alkyl group, a ($C_3$ to $C_6$) cycloalkyl group, a ($C_2$ to $C_4$) alkenyl group, a ($C_1$ to $C_4$) monohydroxyalkyl group, a ($C_2$ to $C_4$) polyhydroxyalkyl group, $G^{25}$ a hydrogen atom, a halogen atom, or a ($C_1$ to $C_4$) alkyl group, with the provision that $G^{24}$ binds in the meta- or ortho-position with respect to the structural fragment $NG^{23}$ of the formula.

Particularly preferred indole derivatives are selected from at least one compound of the group that is constituted from 4-hydroxyindole, 6-hydroxyindole, and 7-hydroxyindole, and physiologically acceptable salts of the aforesaid compounds.

The indoline derivatives usable according to the present specification are preferably selected from at least one compound of formula (K6) and/or from at least one physiologically acceptable salt of a compound in accordance with formula (K6).

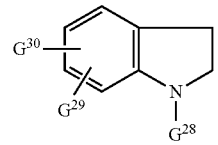

(K6)

In formula (K6):
$G^{28}$ denotes a hydrogen atom, a ($C_1$ to $C_4$) alkyl group, a ($C_3$ to $C_6$) cycloalkyl group, a ($C_2$ to $C_4$) alkenyl group, a ($C_1$ to $C_4$) monohydroxyalkyl group, a ($C_2$ to $C_4$) polyhydroxyalkyl group, an aryl-($C_1$ to $C_4$) alkyl group, $G^{29}$ denotes a hydroxy group or an —$NG^{31}G^{32}$ group, in which $G^{31}$ and $G^{32}$ mutually independently denote a hydrogen atom, a ($C_1$ to $C_4$) alkyl group, a ($C_3$ to $C_6$) cycloalkyl group, a ($C_2$ to $C_4$) alkenyl group, a ($C_1$ to $C_4$) monohydroxyalkyl group, a ($C_2$ to $C_4$) polyhydroxyalkyl group, $G^{30}$ a hydrogen atom, a halogen atom, or a ($C_1$ to $C_4$) alkyl group, In formula (K6) the $G^{29}$ binds in the meta- or ortho-position with respect to structural fragment $NG^{28}$ of the formula.

Particularly preferred indoline derivatives are selected from at least one compound of the group that is constituted from 4-hydroxyindoline, 6-hydroxyindoline, and 7-hydroxyindoline, and physiologically acceptable salts of the aforesaid compounds.

Preferred pyrimidine derivatives are selected from at least one compound of the group that is constituted from 4,6-diaminopyrimidine, 4-amino-2,6-dihydroxypyrimidine, 2,4-diamino-6-hydroxypyrimidine, 2,4,6-trihydroxypyrimidine, 2-amino-4-methylpyrimidine, 2-amino-4-hydroxy-6-methylpyrimidine, and 4,6-dihydroxy-2-methylpyrimidine, and physiologically acceptable salts of the aforesaid compounds.

Coupler components particularly preferred according to the present specification are selected from among m-aminophenol, 5-amino-2-methylphenol, 3-amino-2-chloro-6-methylphenol, 2-hydroxy-4-aminophenoxyethanol, 5-amino-4-chloro-2-methylphenol, 5-(2'-hydroxyethyl)

amino-2-methylphenol, 2,4-dichloro-3-aminophenol, o-aminophenol, m-phenylenediamine, 2-(2,4-diaminophenoxy)ethanol, 1,3-bis(2,4-diaminophenoxy)propane, 1-methoxy-2-amino-4-(2'-hydroxyethylamino)benzene, 1,3-bis(2,4-diaminophenyl)propane, 2,6-bis(2'-hydroxyethylamino)-1-methylbenzene, 2-({3-[(2-hydroxyethyl)amino]-4-methoxy-5-methylphenyl}amino)ethanol, 2-({3-[(2-hydroxyethyl)amino]-2-methoxy-5-methylphenyl}amino)ethanol, 2-({3-[(2-hydroxyethyl)amino]-4,5-dimethylphenyl}amino)ethanol, 2-[3-morpholin-4-ylphenyl)amino]ethanol, 3-amino-4-(2-methoxyethoxy)-5-methylphenylamine, 1-amino-3-bis-(2'-hydroxyethyl)aminobenzene, resorcinol, 2-methylresorcinol, 4-chlororesorcinol, 1,2,4-trihydroxybenzene, 2-amino-3-hydroxypyridine, 3-amino-2-methylamino-6-methoxypyridine, 2,6-dihydroxy-3,4-dimethylpyridine, 3,5-diamino-2,6-dimethoxypyridine, 1-phenyl-3-methylpyrazol-5-one, 1-naphthol, 1,5-dihydroxynaphthalene, 2,7-dihydroxynaphthalene, 1,7-dihydroxynaphthalene, 1,8-dihydroxynaphthalene, 4-hydroxyindole, 6-hydroxyindole, 7-hydroxyindole, 4-hydroxyindoline, 6-hydroxyindoline, 7-hydroxyindoline, or mixtures of these compounds, or physiologically acceptable salts of the aforesaid compounds.

The coupler components are used preferably in a quantity from 0.005 to 20.0 wt %, preferably 0.1 to 5.0 wt %, based in each case on the ready-to-use oxidizing coloring agent.

Developer components and coupler components are generally used in approximately molar quantities with respect to one another. Although molar use has proven useful, a certain excess of individual oxidation dye precursors is not disadvantageous, so that developer components and coupler components can be present at a molar ratio from 1:0.5 to 1:3, in particular 1:1 to 1:2.

Examples of the residues recited as substituents of the compounds of formulas (K1) to (K6) are listed below: Examples of ($C_1$ to $C_4$) alkyl residues are the groups —$CH_3$, —$CH_2CH_3$, —$CH_2CH_2CH_3$, —$CH(CH_3)_2$, —$CH_2CH_2CH_2CH_3$, —$CH_2CH(CH_3)_2$, —$CH(CH_3)CH_2CH_3$, —$C(CH_3)_3$.

Examples according to the present specification of ($C_3$ to $C_6$) cycloalkyl groups are the cyclopropyl, cyclopentyl, and cyclohexyl group. Examples according to the present specification of ($C_1$ to $C_4$) alkoxy residues are —$OCH_3$, —$OCH_2CH_3$, —$OCH_2CH_2CH_3$, —$OCH(CH_3)_2$, —$OCH_2CH_2CH_2CH_3$, —$OCH_2CH(CH_3)_2$, —$OCH(CH_3)CH_2CH_3$, —$OC(CH_3)_3$, in particular a methoxy group or ethoxy group.

Preferred examples of a ($C_1$ to $C_4$) monohydroxyalkyl group that can be mentioned are furthermore —$CH_2OH$, —$CH_2CH_2OH$, —$CH_2CH_2CH_2OH$, —$CH_2CH(OH)CH_3$, —$CH_2CH_2CH_2CH_2OH$, the —$CH_2CH_2OH$ group being preferred.

A particularly preferred example of a ($C_2$ to $C_4$) polyhydroxyalkyl group is the 1,2-dihydroxyethyl group. Examples of halogen atoms are F, Cl, or Br atoms; Cl atoms are very particularly preferred examples. Examples of nitrogen-containing groups are, in particular, —$NH_2$, ($C_1$ to $C_4$) monoalkylamino groups, ($C_1$ to $C_4$) dialkylamino groups, ($C_1$ to $C_4$) trialkylammonium groups, ($C_1$ to $C_4$) monohydroxyalkylamino groups, imidazolinium, and —$NH_3+$. Examples of ($C_1$ to $C_4$) monoalkylamino groups are —$NHCH_3$, —$NHCH_2CH_3$, —$NHCH_2CH_2CH_3$, —$NHCH(CH_3)_2$. Examples of ($C_1$ to $C_4$) dialkylamino group are —$N(CH_3)_2$, —$N(CH_2CH_3)_2$. Examples of ($C_1$ to $C_4$) alkoxy-($C_1$ to $C_4$) alkyl groups are the groups —$CH_2CH_2$—O—$CH_3$, —$CH_2CH_2CH_2$—O—$CH_3$, —$CH_2CH_2$—O—$CH_2CH_3$, —$CH_2CH_2CH_2$—O—$CH_2CH_3$, —$CH_2CH_2$—O—$CH(CH_3)_2$, —$CH_2CH_2CH_2$—O—$CH(CH_3)_2$.

Examples of ($C_1$ to $C_4$) alkoxy-($C_1$ to $C_4$) alkoxy groups are the groups —O—$CH_2CH_2$—O—$CH_3$, —O—$CH_2CH_2CH_2$—O—$CH_3$, —O—$CH_2CH_2$—O—$CH_2CH_3$, —O—$CH_2CH_2CH_2$—O—$CH_2CH_3$, —O—$CH_2CH_2$—O—$CH(CH_3)_2$, —O—$CH_2CH_2CH_2$—O—$CH(CH_3)_2$.

Examples of hydroxy-($C_1$ to $C_4$) alkoxy residues are —O—$CH_2OH$, —O—$CH_2CH_2OH$, —O—$CH_2CH_2CH_2OH$, —O—$CH_2CH(OH)CH_3$, —O—$CH_2CH_2CH_2CH_2OH$.

Examples of ($C_1$ to $C_4$) aminoalkyl residues are —$CH_2NH_2$, —$CH_2CH_2NH_2$, —$CH_2CH_2CH_2NH_2$, —$CH_2CH(NH_2)CH_3$, —$CH_2CH_2CH_2CH_2NH_2$. An example of aryl groups is the phenyl group, which can also be substituted. Examples of aryl-($C_1$ to $C_4$) alkyl groups are the benzyl group and the 2-phenylethyl group.

The agents according to the present specification preferably include, as a color-imparting compound, at least one of the following combinations a) to d) of oxidation dye precursors:

a) at least one heterocyclic developer selected from pyrazole derivatives (in particular 1-(2-hydroxyethyl)pyrazole) and pyrimidine derivatives (in particular 2,4,5,6-tetrahydroxypyrimidone), at least one compound selected from m-aminophenol or derivatives thereof as a coupler,
b) 4-amino-3-methylphenol, 5-amino-2-methylphenol,
c) p-toluylenediamine, 4-amino-3-methylphenol, 5-amino-2-methylphenol,
d) 2-(β-hydroxyethyl)-p-phenylenediamine, 4-amino-3-methylphenol, 5-amino-2-methyl phenol.

The agents according to the present specification include at least one substantive dye. These are dyes that absorb directly onto the hair and do not require an oxidative process for the formation of color. Preferred substantive dyes are nitrophenylenediamines, nitroaminophenols, azo dyes, anthraquinones, or indophenols.

Substantive dyes are respectively used preferably in a quantity from 0.001 to 20.0 wt %, based on the total application preparation. The total quantity of substantive dyes is preferably at most 20.0 wt %.

Substantive dyes can be further subdivided into anionic, cationic, and nonionic substantive dyes.

Anionic substantive dyes: The following are particularly suitable as anionic substantive dyes: 6-hydroxy-5-[(4-sulfophenyl)azo]-2-naphthalenesulfonic acid disodium salt (C.I. 15,985; Food Yellow No. 3; FD&C Yellow No. 6), 2,4-dinitro-1-naphthol-7-sulfonic acid disodium salt (C.I. 10,316; Acid Yellow 1; Food Yellow No. 1), 2-(indane-1,3-dion-2-yl)quinoline-x,x-sulfonic acid (mixture of mono- and disulfonic acid) (C.I. 47,005; D&C Yellow No. 10; Food Yellow No. 13; Acid Yellow 3, Yellow 10), 4-((4-amino-3-sulfophenyl)azo)benzenesulfonic acid disodium salt (C.I. 13,015, Acid Yellow 9), 5-hydroxy-1-(4-sulfophenyl)-4-[(4-sulfophenyl)azo]pyrazole-3-carboxylic acid trisodium salt (C.I. 19,140; Food Yellow No. 4; Acid Yellow 23), 3-[(4-phenylamino)phenyl]azobenzenesulfonic acid sodium salt (C.I. 13,065; Ki406; Acid Yellow 36), 9-(2-carboxyphenyl)-6-hydroxy-3H-xanthen-3-one (C.I. 45,350; Acid Yellow 73; D&C Yellow No. 8), 5-[(2,4-dinitrophenyl)amino]-2-phenylaminobenzenesulfonic acid sodium salt (C.I. 10,385; Acid Orange 3), 4-[(2,4-dihydroxyphenyl)azo]benzenesulfonic acid sodium salt (C.I. 14,270; Acid Orange 6), 4-[(2-hydroxynaphth-1-yl)azo]-benzenesulfonic acid sodium salt (C.I. 15,510; Acid Orange 7), 4-[(2,4-dihydroxy-3-[(2,4-dimethylphenyl)azo]phenyl)azo]benzenesulfonic acid sodium salt (C.I. 20,170; Acid Orange 24), 4-hydroxy-3-[(2-methoxyphenyl)azo]-1-naphthalenesulfonic acid sodium salt (C.I. 14,710; Acid Red 4), 4-hydroxy-3-[(4-sulfonaphth-1-yl)azo]-1-naphthalenesulfonic acid disodium salt (C.I. 14,720; Acid Red No. 14), 6-hydroxy-5-[(4-sulfonaphth-1-yl)azo]-2,4-naphthalenedisulfonic acid trisodium salt (C.I. 16,255; Ponceau 4R; Acid Red 18), 3-hydroxy-4-[(4-sulfonaphth-1-yl)azo]-2,7-naphthalenedisulfonic acid trisodium salt (C.I. 16,185; Acid Red 27), 8-amino-1-hydroxy-2-(phenylazo)-3,6-naphthalenedisulfonic acid disodium salt (C.I. 17,200; Acid Red 33; Red 33), 5-(acetylamino)-4-hydroxy-3-[(2-methylphenyl)azo]-2,7-naphthalenedisulfonic acid disodium salt (C.I. 18,065; Acid Red 35), 2-(3-hydroxy-2,4,5,7-tetraiodo-dibenzopyran-6-on-9-yl)benzoic acid disodium salt (C.I. 45,430; Acid Red 51), N-[6-(diethylamino)-9-(2,4-disulfophenyl)-3H-xanthen-3-ylidene]-N-ethylethanammonium hydroxide, internal salt, sodium salt (C.I. 45,100; Acid Red 52), 8-[(4-(phenylazo)phenyl)azo]-7-naphthol-1,3-disulfonic acid disodium salt (C.I. 27,290; Acid Red 73), 2',4',5',7'-tetrabromo-3',6'-dihydroxyspiro[isobenzofuran-1(3H),9'-[9H]xanthen]-3-one disodium salt (C.I. 45,380; Acid Red 87), 2',4',5',7'-tetrabromo-4,5,6,7-tetrachloro-3',6'-dihydroxyspiro[isobenzofuran-1(3H),9'[9H]xanthen]-3-one disodium salt (C.I. 45,410; Acid Red 92), 3',6'-dihydroxy-4',5'-diiodospiro[isobenzofuran-1(3H),9'(9H)xanthen]-3-one disodium salt (C.I. 45425; Acid Red 95), 2-hydroxy-3-((2-hydroxynaphth-1-yl)azo]-5-nitrobenzenesulfonic acid sodium salt (C.I. 15,685; Acid Red 184), 3-hydroxy-4-(3-methyl-5-oxo-1-phenyl-4,5-dihydro-1H-pyrazol-4-ylazo) naphthalene-1-sulfonic acid sodium salt, chromium complex (Acid Red 195), 3-hydroxy-4-[(4-methyl-2-sulfonophenyl) azo]-2-naphthalenecarboxylic acid calcium salt (C.I. 15,850:1; Pigment Red 57:1), 3-[(2,4-dimethyl-5-sulfophenyl)azo]-4-hydroxy-1-naphthalenesulfonic acid disodium salt (C.I. 14,700; Food Red No. 1; Ponceau SX; FD&C Red No. 4), 1,4-bis[(2-sulfo-4-methylphenyl)amino]-9,10-anthraquinone disodium salt (C.I. 61,570; Acid Green 25), bis [4-(dimethylamino)phenyl]-(3,7-disulfo-2-hydroxynaphth-1-yl)carbenium internal salt, sodium salt (C.I. 44,090; Food Green No. 4; Acid Green 50), bis[4-(diethylamino)-phenyl] (2,4-disulfophenyl)carbenium internal salt, sodium salt (2:1) (C.I. 42,045; Food Blue No. 3; Acid Blue 1), bis[4-(diethylamino)phenyl](5-hydroxy-2,4-disulfophenyl)carbenium internal salt, calcium salt (2:1) (C.I. 42,051; Acid Blue 3), N-[4-[(2,4-disulfophenyl)[4-[ethyl(phenylmethyl)amino] phenyl]methylene]-2,5-cyclohexadien-1-ylidene]-N-ethylbenzenemethanaminium hydroxide, internal salt, sodium salt (C.I. 42,080; Acid Blue 7), (2-sulfophenyl)di[4-(ethyl((4-sulfophenyl)methyl)amino)phenyl]carbenium disodium salt betaine (C.I. 42,090; Acid Blue 9; FD&C Blue No. 1), 1-amino-4-(phenylamino)-9,10-anthraquinone-2-sulfonic acid (C.I. 62,055; Acid Blue 25), 1-amino-4-(cyclohexylamino)-9,10-anthraquinone-2-sulfonic acid sodium salt (C.I. 62045; Acid Blue 62), 2-(1,3-dihydro-3-oxo-5-sulfo-2H-indol-2-ylidene)-2,3-dihydro-3-oxo-1H-indole-5-sulfonic acid disodium salt (C.I. 73,015; Acid Blue 74), 9-(2-carboxyphenyl)-3-[(2-methylphenyl)amino]-6-[(2-methyl-4-sulfophenyl)amino]xanthylium internal salt, sodium salt (C.I. 45,190; Acid Violet 9), 1-hydroxy-4-[(4-methyl-2-sulfophenyl)amino]-9,10-anthraquinone sodium salt (C.I. 60,730; D&C Violet No. 2; Acid Violet 43), bis[3-nitro-4-[(4-phenylamino)-3-sulfophenylamino]-phenyl]sulfone (C.I. 10,410; Acid Brown 13), 5-amino-4-hydroxy-6-[(4-nitrophenyl)-azo]-3-(phenylazo)-2,7-naphthalenedisulfonic acid disodium salt (C.I. 20,470; Acid Black 1), 3-hydroxy-4-[(2-hydroxynaphth-1-yl)azo]-7-nitro-1-naphthalenesulfonic acid chromium complex (3:2) (C.I. 15,711; Acid Black 52), 4-(acetylamino)-5-hydroxy-6-[(7-sulfo-4-[(4-sulfophenyl) azo]naphth-1-yl)azo]-1,7-naphthalenedisulfonic acid tetrasodium salt (C.I. 28,440; Food Black No. 1), 3',3",5',5"-tetrabromophenolsulfonephthalein (bromophenol blue), 3,4,5,6,3',3",5',5"-octabromophenolsulfonephthalein (tetrabromophenol blue). Preferred anionic substantive dyes are the compounds known by the international names or trade names Acid Yellow 1, Yellow 10, Acid Yellow 23, Acid Yellow 36, Acid Orange 7, Acid Red 33, Acid Red 52, Pigment Red 57:1, Acid Blue 7, Acid Green 50, Acid Violet 43, Acid Black 1, and Acid Black 52.

Cationic substantive dyes: The following are suitable in particular as cationic substantive dyes: 9-(dimethylamino)-benzo[a]phenoxazin-7-ium chloride (C.I. 51,175; Basic Blue 6), di[4-(diethylamino)phenyl][4-(ethylamino)naphthyl]carbenium chloride (C.I. 42,595; Basic Blue 7), di-(4-(dimethylamino)phenyl)-(4-(methylphenylamino)naphthalene-1-yl) carbenium chloride (C.I. 42,563; Basic Blue 8), 3,7-di (dimethylamino)phenothiazin-5-ium chloride (C.I. 52,015 Basic Blue 9), di[4-(dimethylamino)phenyl][4-(phenylamino)naphthyl]carbenium chloride (C.I. 44,045; Basic Blue 26), 2-[(4-(ethyl(2-hydroxyethyl)amino)phenyl)azo]-6-methoxy-3-methylbenzothiazolium methyl sulfate (C.I. 11,154; Basic Blue 41), 8-amino-2-bromo-5-hydroxy-4-imino-6-[(3-(trimethylammonio)phenyl)amino]-1(4H)-naphthalenone chloride (C.I. 56,059; Basic Blue No. 99), bis[4-(dimethylamino)phenyl]-[4-(methylamino)phenyl] carbenium chloride (C.I. 42,535; Basic Violet 1), tri(4-amino-3-methylphenyl)carbenium chloride (C.I. 42,520; Basic Violet 2), tri[4-(dimethylamino)phenyl]carbenium chloride (C.I. 42,555; Basic Violet 3), 2-[3,6-(diethylamino)dibenzopyranium-9-yl]benzoic acid chloride (C.I. 45,170; Basic Violet 10), di(4-aminophenyl)(4-amino-3-methylphenyl)carbenium chloride (C.I. 42,510, Basic Violet 14), 1,3-bis[(2,4-diamino-5-methylphenyl)azo]-3-methylbenzene (C.I. 21,010; Basic Brown 4), 1-[(4-aminophenyl)azo]-7-(trimethylammonio)-2-naphthol chloride (C.I. 12,250; Basic Brown 16), 1-[(4-amino-2-nitrophenyl)azo]-7-(trimethylammonio)-2-naphthol chloride, 1-[(4-amino-3-nitrophenyl) azo]-7-(trimethylammonio)-2-naphthol chloride (C.I. 12,251; Basic Brown 17), 3-[(4-amino-2,5-dimethoxyphenyl)azo]-N,N,N-trimethylbenzenaminium chloride (C.I. 12,605, Basic Orange 69), 3,7-diamino-2,8-dimethyl-5-phenylphenazinium chloride (C.I. 50,240; Basic Red 2), 1,4-dimethyl-5-[(4-(dimethylamino)phenyl)azo]-1,2,4-triazolium chloride (C.I. 11,055; Basic Red 22), 2-hydroxy-1-[(2-methoxyphenyl)azo]-7-(trimethylammonio)naphthalene chloride (C.I. 12,245; Basic Red 76), di[4-(dimethylamino) phenyl]iminomethane hydrochloride (C.I. 41,000; Basic Yellow 2), 2-[2-((2,4-dimethoxyphenyl)amino)ethenyl]-1,3,3-trimethyl-3H-indol-1-ium chloride (C.I. 48,055; Basic Yellow 11), 3-methyl-1-phenyl-4-[(3-(trimethylammonio) phenyl)azo]pyrazol-5-one chloride (C.I. 12,719; Basic Yellow 57), bis[4-(diethylamino)phenyl]phenylcarbenium hydrogen sulfate (1:1) (C.I. 42,040; Basic Green 1), di(4-(dimethylamino)phenyl)phenylmethanol (C.I. 42,000; Basic Green 4), 1-(2-morpholiniumpropylamino)-4-hydroxy-9,10-anthraquinone methyl sulfate, 1-[(3-(dimethylpropylaminium)propyl)amino]-4-(methylamino)-9,10-anthraquinone chloride, and substantive dyes that include a heterocycle which comprises at least one quaternary nitrogen atom.

Preferred cationic substantive dyes are, in this context
(a) cationic triphenylmethane dyes, for example Basic Blue 7, Basic Blue 26, Basic Violet 2, and Basic Violet 14,
(b) aromatic systems that are substituted with a quaternary nitrogen group, for example Basic Yellow 57, Basic Red 76, Basic Blue 99, Basic Brown 16, and Basic Brown 17, and (c) substantive dyes that include a heterocycle which comprises at least one quaternary nitrogen atom, as recited for example in EP-A2-998 908, to which reference is explicitly made here, in claims 6 to 11.

Preferred cationic substantive dyes of group (c) are, in particular, the following compounds:

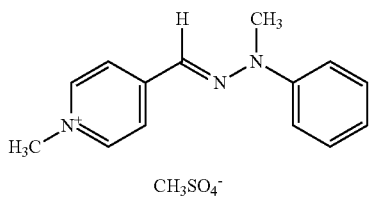

(DZ1)

CH₃SO₄⁻

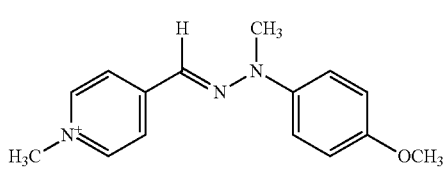

(DZ2)

Cl⁻

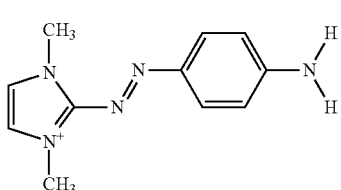

(DZ3)

Cl⁻

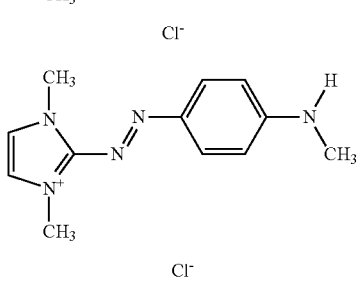

(DZ4)

Cl⁻

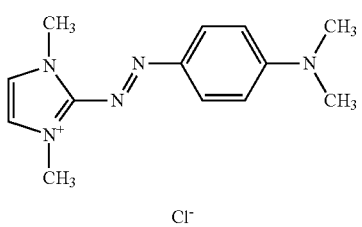

(DZ5)

Cl⁻

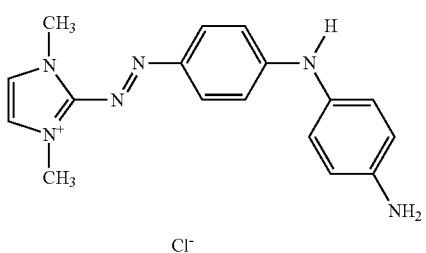

(DZ6)

Cl⁻

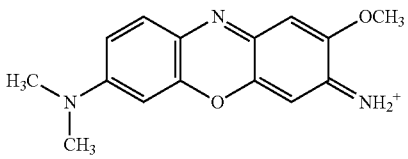

(DZ7)

Cl⁻

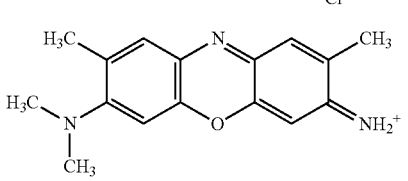

(DZ8)

Cl⁻

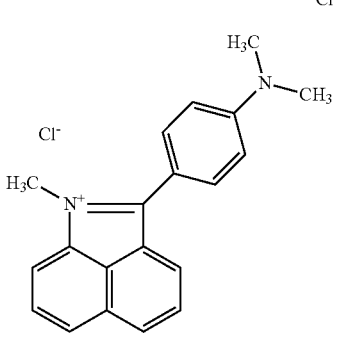

(DZ9)

The compounds of formulas (DZ1), (DZ3), and (DZ5), which are also known by the names Basic Yellow 87, Basic Orange 31, and Basic Red 51, are very particularly preferred cationic substantive dyes of group (c).

The cationic substantive dyes that are marketed under the trade name ARIANOR® are likewise very particularly preferred cationic substantive dyes according to the present specification.

Nonionic substantive dyes: Nonionic nitro dyes and quinone dyes, and neutral azo dyes, are suitable in particular as nonionic substantive dyes.

Suitable blue nitro dyes are, in particular: 1,4-bis[(2-hydroxyethyl)amino]-2-nitrobenzene, 1-(2-hydroxyethyl) amino-2-nitro-4-[di(2-hydroxyethyl)amino]benzene (HC Blue 2), 1-methylamino-4-[methyl-(2,3-dihydroxypropyl) amino]-2-nitrobenzene (HC Blue 6),1-[(2,3-dihydroxypropyl)amino]-4-[ethyl-(2-hydroxyethyl)amino]-2-nitrobenzene hydrochloride (HC Blue 9), 1-[(2,3-dihydroxypropyl) amino]-4-[methyl-(2-hydroxyethyl)amino]-2-nitrobenzene (HC Blue 10), 4-[di(2-hydroxyethyl)amino]-1-[(2-methoxyethyl)amino]-2-nitrobenzene (HC Blue 11), 4-[ethyl-(2-hydroxyethyl)amino]-1-[(2-hydroxyethyl)amino]-2-nitrobenzene hydrochloride (HC Blue 12), 2-((4-amino-2-nitrophenyl)amino)-5-dimethylaminobenzoic acid (HC Blue 13), 1-amino-3-methyl-4-[(2-hydroxyethyl)amino]-6-nitrobenzene (HC Violet 1), 1-(3-hydroxypropylamino)-4-[di (2-hydroxyethyl)amino]-2-nitrobenzene (HC Violet 2), 1-(2-aminoethylamino)-4-[di(2-hydroxyethyl)amino]-2-nitrobenzene, 4-(di(2-hydroxyethyl)amino)-2-nitro-1-phenylaminobenzene.

Suitable red nitro dyes are, in particular: 1-amino-4-[(2-hydroxyethyl)amino]-2-nitrobenzene (HC Red 7), 2-amino-4,6-dinitrophenol (picramic acid) and salts thereof, 1,4-diamino-2-nitrobenzene (C.I. 76,070), 4-amino-2-nitrodiphenylamine (HC Red 1), 1-amino-4-[di(2-hydroxyethyl)amino]-2-nitrobenzene hydrochloride (HC Red 13), 1-amino-4-[(2-hydroxyethyl)amino]-5-chloro-2-nitrobenzene, 4-amino-1-[(2-hydroxyethyl)amino]-2-nitrobenzene (HC Red 3), 4-[(2-hydroxyethyl)methylamino]-1-(methylamino)-2-nitrobenzene, 1-amino-4-[(2,3-dihydroxypropyl)amino]-5-methyl-2-nitrobenzene, 1-amino-4-(methylamino)-2-nitrobenzene, 4-amino-2-nitro-1-[(prop-2-en-1-yl)amino]benzene, 4-amino-3-nitrophenol, 4-[(2-hydroxyethyl)amino]-3-nitrophenol, 4-[(2-nitrophenyl)amino]phenol (HC Orange 1), 1-[(2-aminoethyl)amino]-4-(2-hydroxyethoxy)-2-nitrobenzene (HC Orange 2), 4-(2,3-dihydroxypropoxy)-1-[(2-hydroxyethyl)amino]-2-nitrobenzene (HC Orange 3), 1-amino-5-chloro-4-[(2,3-dihydroxypropyl)amino]-2-nitrobenzene (HC Red 10), 5-chloro-1,4-[di(2,3-dihydroxypropyl)amino]-2-nitrobenzene (HC Red 11), 2-[(2-hydroxyethyl)amino]-4,6-dinitrophenol, 4-ethylamino-3-nitrobenzoic acid, 2-[(4-amino-2-nitrophenyl)amino]benzoic acid, 2-chloro-6-ethylamino-4-nitrophenol, 2-amino-6-chloro-4-nitrophenol, 4-[(3-hydroxypropyl)amino]-3-nitrophenol (HC Red BN), 2,5-diamino-6-nitropyridine, 6-amino-3-[(2-hydroxyethyl)amino]-2-nitropyridine, 3-amino-6-[(2-hydroxyethyl)amino]-2-nitropyridine, 3-amino-6-(ethylamino)-2-nitropyridine, 3-[(2-hydroxyethyl)amino]-6-(methylamino)-2-nitropyridine, 3-amino-6-(methylamino)-2-nitropyridine, 6-(ethylamino)-3-[(2-hydroxyethyl)amino]-2-nitropyridine, 1,2,3,4-tetrahydro-6-nitroquinoxaline, 7-amino-3,4-dihydro-6-nitro-2H-1,4-benzoxazine (HC Red 14).

Suitable yellow nitro dyes are, in particular: 1,2-diamino-4-nitrobenzene (C.I. 76,020), 1-[(2-hydroxyethyl)amino]-2-nitrobenzene (HC Yellow 2), 1-(2-hydroxyethoxy)-2-[(2-hydroxyethyl)amino]-5-nitrobenzene (HC Yellow 4), 1-amino-2-[(2-hydroxyethyl)amino]-5-nitrobenzene (HC Yellow 5), 4-[(2,3-dihydroxypropyl)amino]-3-nitro-1-trifluoromethylbenzene (HC Yellow 6), 2-[di(2-hydroxyethyl)amino]-5-nitrophenol, 2-[(2-hydroxyethyl)amino]-1-methoxy-5-nitrobenzene, 2-amino-3-nitrophenol, 2-amino-4-nitrophenol, 1-amino-2-methyl-6-nitrobenzene, 1-(2-hydroxyethoxy)-3-methylamino-4-nitrobenzene, 2,3-(dihydroxypropoxy)-3-methylamino-4-nitrobenzene, 3-[(2-aminoethyl)amino]-1-methoxy-4-nitrobenzene hydrochloride (HC Yellow 9), 1-chloro-2,4-bis[(2-hydroxyethyl)amino]-5-nitrobenzene (HC Yellow 10), 2-[(2-hydroxyethyl)amino]-5-nitrophenol (HC Yellow 11), 1-[(2'-ureidoethyl)amino]-4-nitrobenzene, 1-amino-4-[(2-aminoethyl)amino]-5-methyl-2-nitrobenzene, 4-[(2-hydroxyethyl)amino]-3-nitro-1-methylbenzene, 1-chloro-4-[(2-hydroxyethyl)amino]-3-nitrobenzene (HC Yellow 12), 4-[(2-hydroxyethyl)amino]-3-nitro-1-trifluoromethylbenzene (HC Yellow 13), 4-[(2-hydroxyethyl)amino]-3-nitrobenzonitrile (HC Yellow 14), 4-[(2-hydroxyethyl)amino]-3-nitrobenzamide (HC Yellow 15) 3-[(2-hydroxyethyl)amino]-4-methyl-1-nitrobenzene, 4-chloro-3-[(2-hydroxyethyl)amino]-1-nitrobenzene.

Suitable quinone dyes are, in particular: 1,4-di[(2,3-dihydroxypropyl)amino]-9,10-anthraquinone, 1,4-di[(2-hydroxyethyl)amino]-9,10-anthraquinone (C.I. 61,545, Disperse Blue 23), 1-[(2-hydroxyethyl)amino]-4-methylamino-9,10-anthraquinone (C.I. 61,505, Disperse Blue 3), 2-[(2-aminoethyl)amino]-9,10-anthraquinone (HC Orange 5), 1-amino-4-hydroxy-9,10-anthraquinone (C.I. 60,710, Disperse Red 15), 1-hydroxy-4-[(4-methyl-2-sulfophenyl)amino]-9,10-anthraquinone, 7-beta-D-glucopyranosyl-9,10-dihydro-1-methyl-9,10-dioxo-3,5,6,8-tetrahydroxy-2-anthracenecarboxylic acid (C.I. 75,470, Natural Red 4), 1-[(3-aminopropyl)amino]-4-methylamino-9,10-anthraquinone (HC Blue 8), 1[(3-aminopropyl)amino]-9,10-anthraquinone (HC Red 8), 1,4-diamino-2-methoxy-9,10-anthraquinone (C.I. 62,015, Disperse Red 11, Solvent Violet No. 26), 1,4-dihydroxy-5,8-bis[(2-hydroxyethyl)amino]-9,10-anthraquinone (C.I. 62,500, Disperse Blue 7, Solvent Blue No. 69), 1,4-diamino-9,10-anthraquinone (C.I. 61,100, Disperse Violet 1), 1-amino-4-(methylamino)-9,10-anthraquinone (C.I. 61,105, Disperse Violet 4, Solvent Violet No. 12), 2-hydroxy-3-methoxy-1,4-naphthoquinone, 2,5-dihydroxy-1,4-naphthoquinone, 2-hydroxy-3-methyl-1,4-naphthoquinone, N-{6-[(3-chloro-4-(methylamino)phenyl)imino]-4-methyl-3-oxo-1,4-cyclohexadien-1-yl}urea (HC Red 9), 2-{{4-[di(2-hydroxyethyl)amino]phenyl}amino}-5-[(2-hydroxyethyl)amino]-2,5-cyclohexadiene-1,4-dione (HC Green 1), 5-hydroxy-1,4-naphthoquinone (C.I. 75,500, Natural Brown 7), 2-hydroxy-1,4-naphthoquinone (C.I. 75,480, Natural Orange 6), 1,2-dihydro-2-(1,3-dihydro-3-oxo-2H-indol-2-yliden)-3H-indol-3-one (C.I. 73,000), 4-{{5-[(2-hydroxyethyl)amino]-1-methyl-1H-pyrazol-4-yl}imino}-4,5-dihydro-5-[(2-hydroxyethyl)imino]-1-methyl-1H-pyrazole sulfate (1:1), hydrate (1:1).

Suitable neutral azo dyes are, in particular: 1-[di(2-hydroxyethyl)amino]-3-methyl-4-[(4-nitrophenyl)azo]benzene (C.I. 11,210, Disperse Red 17), 1-[di(2-hydroxyethyl)amino]-4-[(4-nitrophenyl)azo]benzene (Disperse Black 9), 4-[(4-aminophenyl)azo]-1-[di(2-hydroxyethyl)amino]-3-methylbenzene (HC Yellow 7), 2,6-diamino-3-[(pyridin-3-yl)azo]pyridine, 2-{[4-(acetylamino)phenyl]azo}-4-methylphenol (C.I. 11855; Disperse Yellow 3), 4-[(4-nitrophenyl)azo]aniline (C.I. 11,005; Disperse Orange 3).

Preferred nonionic substantive dyes are the compounds known by the international names or commercial names HC Yellow 2, HC Yellow 4, HC Yellow 5, HC Yellow 6, HC Yellow 12, HC Orange 1, Disperse Orange 3, HC Red 1, HC Red 3, HC Red 10, HC Red 11, HC Red 13, HC Red BN, HC Blue 2, HC Blue 11, HC Blue 12, Disperse Blue 3, HC Violet 1, Disperse Violet 1, Disperse Violet 4, Disperse Black 9, as well as 1,4-diamino-2-nitrobenzene, 2-amino-4-nitrophenol, 1,4-bis-(2-hydroxyethyl)amino-2-nitrobenzene, 3-nitro-4-(2-hydroxyethyl)aminophenol, 2-(2-hydroxyethyl)amino-4,6-dinitrophenol, 4-[(2-hydroxyethyl)amino]-3-nitro-1-methylbenzene, 1-amino-4-(2-hydroxyethyl)amino-5-chloro-2-nitrobenzene, 4-amino-3-nitrophenol, 1-(2'-ureidoethyl)amino-4-nitrobenzene, 2-[(4-amino-2-nitrophenyl)amino]benzoic acid, 6-nitro-1,2,3,4-tetrahydroquinoxaline, 2-hydroxy-1,4-naphthoquinone, picramic acid and salts thereof, 2-amino-6-chloro-4-nitrophenol, 4-ethylamino-3-nitrobenzoic acid, and 2-chloro-6-ethylamino-4-nitrophenol.

It is not necessary for the substantive dyes to represent uniform compounds in each case. Instead, depending on the manufacturing methods for the individual dyes, further components can also be included in subordinate quantities if they do not disadvantageously influence the color result or need not be excluded for other (e.g. toxicological) reasons.

Naturally occurring dyes, such as those included e.g. in red henna, neutral henna, black henna, chamomile blossoms, sandalwood, black tea, buckthorn bark, salvia, logwood, madder root, catechu, Spanish cedar, and alkanna root, can also be used as substantive dyes.

It is preferred to use, as color-imparting compounds of the precursors of bioanalogous dyes, those indoles and indolines which comprise at least two groups selected from hydroxy and/or amino groups, preferably as a substituent on the six-membered ring. These groups can carry further substituents, for example in the form of an etherification or esterification of the hydroxy group, or an alkylation of the amino group. In a further embodiment, the coloring agents include at least one indole derivative and/or indoline derivative. Compositions according to the present specification that include precursors of bioanalogous dyes are preferably used as air-oxidizing coloring agents. In this embodiment, the aforesaid compositions consequently do not have an additional oxidizing agent added to them.

Particularly suitable as precursors of bioanalogous hair dyes are derivatives of 5,6-dihydroxyindoline of formula (RN1).

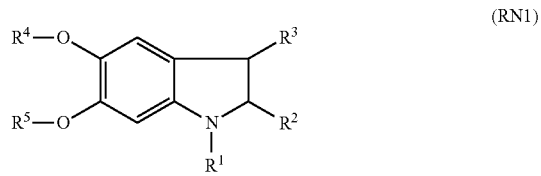

(RN1)

In formula (RN1), mutually independently:
$R^1$ denotes hydrogen, a $C_1$ to $C_4$ alkyl group, or a $C_1$ to $C_4$ hydroxyalkyl group,
$R^2$ denotes hydrogen or a —COOH group, wherein the —COOH group can also be present as a salt with a physiologically acceptable cation,
$R^3$ denotes hydrogen or a $C_1$ to $C_4$ alkyl group,
$R^4$ denotes hydrogen, a $C_1$ to $C_4$ alkyl group, or a —CO—$R^6$ group in which $R^6$ denotes a $C_1$ to $C_4$ alkyl group, and
$R^5$ denotes one of the groups recited under $R^4$,
as well as physiologically acceptable salts of these compounds with an organic or inorganic acid.

Particularly preferred derivatives of indoline are 5,6-dihydroxyindoline, N-methyl-5,6-dihydroxyindoline, N-ethyl-5,6-dihydroxyindoline, N-propyl-5,6-dihydroxyindoline, N-butyl-5,6-dihydroxyindoline, and 5,6-dihydroxyindoline-2-carboxylic acid.

Particularly to be emphasized within this group are N-methyl-5,6-dihydroxyindoline, N-ethyl-5,6-dihydroxyindoline, N-propyl-5,6-dihydroxyindoline, N-butyl-5,6-dihydroxyindoline, and in particular 5,6-dihydroxyindoline.

Also outstandingly suitable as precursors of bioanalogous hair dyes are derivatives of 5,6-dihydroxyindole of formula (RN2).

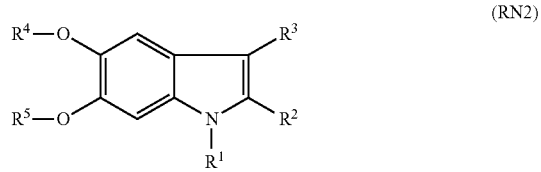

(RN2)

In formula (RN2), mutually independently:
$R^1$ denotes hydrogen, a $C_1$ to $C_4$ alkyl group, or a $C_1$ to $C_4$ hydroxyalkyl group,
$R^2$ denotes hydrogen or a —COOH group, where the —COOH group can also be present as a salt with a physiologically acceptable cation,
$R^3$ denotes hydrogen or a $C_1$ to $C_4$ alkyl group,
$R^4$ denotes hydrogen, a $C_1$ to $C_4$ alkyl group, or a —CO—$R^6$ group in which $R^6$ denotes a $C_1$ to $C_4$ alkyl group, and
$R^5$ denotes one of the groups recited under $R^4$,
as well as physiologically acceptable salts of these compounds with an organic or inorganic acid.

Particularly preferred derivatives of indole are 5,6-dihydroxyindole, N-methyl-5,6-dihydroxyindole, N-ethyl-5,6-dihydroxyindole, N-propyl-5,6-dihydroxyindole, N-butyl-5,6-dihydroxyindole, 5,6-dihydroxyindole-2-carboxylic acid.

To be emphasized within this group are N-methyl-5,6-dihydroxyindole, N-ethyl-5,6-dihydroxyindole, N-propyl-5,6-dihydroxyindole, N-butyl-5,6-dihydroxyindole, and in particular 5,6-dihydroxyindole.

The indoline derivatives or indole derivatives can be used both as free bases and in the form of their physiologically acceptable salts with inorganic or organic acids, e.g. hydrochlorides, sulfates, and hydrobromides.

It is preferred according to the present specification if the cosmetic agent includes the aforesaid starch modified by means of propylene oxide in a quantity from 0.01 wt % to 20.0 wt %, particularly preferably from 0.01 wt % to 10.0 wt %, very particularly preferably from 0.1 wt % to 5.0 wt %, most preferably from 0.1 to 2.0 wt %, based in each case on the weight of the agent.

The starches, modified by means of propylene oxide, of the first subject of the present specification that are characterized as preferred are preferably included in the cosmetic agent.

Cosmetic agents very particularly preferred according to the present specification conform to at least one of the following examples A) to R):

A): A cosmetic agent for coloring keratinic fibers, in particular human hair, including in a cosmetic carrier at least one color-imparting compound and at least one uncrosslinked starch, modified by means of propylene oxide, that has an average molecular weight (weight-average) from 50 to 2500 kDa and a propylene oxide content from 2.0 to 12.0 wt % (based on the weight of the starch modified by means of propylene oxide).

B): A cosmetic agent for coloring keratinic fibers, in particular human hair, including in a cosmetic carrier at least one color-imparting compound and at least one starch, modified by means of propylene oxide, that has an average molecular weight (weight-average) from 700 to 1000 kDa and a propylene oxide content from 2.0 to 12.0 wt % (based on the weight of the starch modified by means of propylene oxide).

C): A cosmetic agent for coloring keratinic fibers, in particular human hair, including in a cosmetic carrier at least one color-imparting compound and at least one starch, modified by means of propylene oxide, that has an average molecular weight (weight-average) from 50 to 2500 kDa, a propylene oxide content from 2.0 to 12.0 wt % (based on the weight of the starch modified by means of propylene oxide), and a viscosity from 3000 to 200,000 mPas (in 43-wt % aqueous solution, Brookfield viscometer, spindle 7, at 20° C. and 20 rpm).

D): A cosmetic agent for coloring keratinic fibers, in particular human hair, including in a cosmetic carrier at least one color-imparting compound and at least one starch, modified by means of propylene oxide, that has an average molecular weight (weight-average) from 50 to 2500 kDa, a propylene oxide content from 2.0 to 12.0 wt % (based on the weight of the starch modified by means of propylene oxide), and a viscosity from 1000 to 100,000 mPas (in 43-wt % aqueous solution, Brookfield viscometer, spindle 7, at 20° C. and 20 rpm).

E): A cosmetic agent for coloring keratinic fibers, in particular human hair, including in a cosmetic carrier at least one color-imparting compound and at least one starch, modified by means of propylene oxide, that has an average molecular weight (weight-average) from 700 to 1000 kDa, a propylene oxide content from 2.0 to 12.0 wt % (based on the weight of the starch modified by means of propylene oxide), and a viscosity from 3000 to 200,000 mPas (in 43-wt % aqueous solution, Brookfield viscometer, spindle 7, at 20° C. and 20 rpm).

F): A cosmetic agent for coloring keratinic fibers, in particular human hair, including in a cosmetic carrier at least one color-imparting compound and at least one starch, modified by means of propylene oxide, that has an average molecular weight (weight-average) from 700 to 1000 kDa, a propylene oxide content from 2.0 to 12.0 wt % (based on the weight of the starch modified by means of propylene oxide), and a viscosity from 10,000 to 100,000 mPas (in 43-wt % aqueous solution, Brookfield viscometer, spindle 7, at 20° C. and 20 rpm).

G): A cosmetic agent for coloring keratinic fibers, in particular human hair, including in a cosmetic carrier at least one color-imparting compound and at least one uncrosslinked starch, modified by means of propylene oxide, selected from tapioca starch, potato starch, corn starch, or mixtures, wherein said modified starch has an average molecular weight (weight-average) from 50 to 2500 kDa and a propylene oxide content from 2.0 to 12.0 wt % (based on the weight of the starch modified by means of propylene oxide).

H): A cosmetic agent for coloring keratinic fibers, in particular human hair, including in a cosmetic carrier at least one color-imparting compound and at least one starch, modified by means of propylene oxide, selected from tapioca starch, potato starch, corn starch, or mixtures, wherein said modified starch has an average molecular weight (weight-average) from 700 to 1000 kDa and a propylene oxide content from 2.0 to 12.0 wt % (based on the weight of the starch modified by means of propylene oxide).

I): A cosmetic agent for coloring keratinic fibers, in particular human hair, including in a cosmetic carrier at least one color-imparting compound and at least one starch, modified by means of propylene oxide, selected from tapioca starch, potato starch, corn starch, or mixtures, wherein said modified starch has an average molecular weight (weight-average) from 50 to 2500 kDa, a propylene oxide content from 2.0 to 12.0 wt % (based on the weight of the starch modified by means of propylene oxide), and a viscosity from 3,000 to 200,000 mPas (in 43-wt % aqueous solution, Brookfield viscometer, spindle 7, at 20° C. and 20 rpm).

J): A cosmetic agent for coloring keratinic fibers, in particular human hair, including in a cosmetic carrier at least one color-imparting compound and at least one starch, modified by means of propylene oxide, selected from tapioca starch, potato starch, corn starch, or mixtures, wherein said modified starch has an average molecular weight (weight-average) from 50 to 2500 kDa, a propylene oxide content from 2.0 to 12.0 wt % (based on the weight of the starch modified by means of propylene oxide), and a viscosity from 1000 to 100,000 mPas (in 43-wt % aqueous solution, Brookfield viscometer, spindle 7, at 20° C. and 20 rpm).

K): A cosmetic agent for coloring keratinic fibers, in particular human hair, including in a cosmetic carrier at least one color-imparting compound and at least one starch, modified by means of propylene oxide, selected from tapioca starch, potato starch, corn starch, or mixtures, wherein said modified starch has an average molecular weight (weight-average) from 700 to 1000 kDa, a propylene oxide content from 2.0 to 12.0 wt % (based on the weight of the starch modified by means of propylene oxide), and a viscosity from 3000 to 200,000 mPas (in 43-wt % aqueous solution, Brookfield viscometer, spindle 7, at 20° C. and 20 rpm).

L): A cosmetic agent for coloring keratinic fibers, in particular human hair, including in a cosmetic carrier at least one color-imparting compound and at least one starch, modified by means of propylene oxide, selected from tapioca starch, potato starch, corn starch, or mixtures, wherein said modified starch has an average molecular weight (weight-average) from 700 to 1000 kDa, a propylene oxide content from 2.0 to 12.0 wt % (based on the weight of the starch modified by means of propylene oxide), and a viscosity from 10,000 to 100,000 mPas (in 43-wt % aqueous solution, Brookfield viscometer, spindle 7, at 20° C. and 20 rpm).

M): A cosmetic agent for coloring keratinic fibers, in particular human hair, including in a cosmetic carrier at least one color-imparting compound and at least one uncrosslinked tapioca starch, modified by means of propylene oxide, that has an average molecular weight (weight-average) from 50 to 2500 kDa and a propylene oxide content from 2.0 to 12.0 wt % (based on the weight of the tapioca starch modified by means of propylene oxide).

N): A cosmetic agent for coloring keratinic fibers, in particular human hair, including in a cosmetic carrier at least one color-imparting compound and at least one tapioca starch, modified by means of propylene oxide, that has an average molecular weight (weight-average) from 700 to 1000 kDa and a propylene oxide content from 2.0 to 12.0 wt % (based on the weight of the tapioca starch modified by means of propylene oxide).

O): A cosmetic agent for coloring keratinic fibers, in particular human hair, including in a cosmetic carrier at least one color-imparting compound and at least one tapioca starch, modified by means of propylene oxide, that has an average molecular weight (weight-average) from 50 to 2500 kDa, a propylene oxide content from 2.0 to 12.0 wt % (based on the weight of the tapioca starch modified by means of propylene oxide), and a viscosity from 3000 to 200,000 mPas (in 43-wt % aqueous solution, Brookfield viscometer, spindle 7, at 20° C. and 20 rpm).

P): A cosmetic agent for coloring keratinic fibers, in particular human hair, including in a cosmetic carrier at least one color-imparting compound and at least one tapioca starch, modified by means of propylene oxide, that has an average molecular weight (weight-average) from 50 to 2500 kDa, a propylene oxide content from 2.0 to 12.0 wt % (based on the weight of the tapioca starch modified by means of propylene oxide), and a viscosity from 1000 to 100,000 mPas (in 43-wt % aqueous solution, Brookfield viscometer, spindle 7, at 20° C. and 20 rpm).

Q): A cosmetic agent for coloring keratinic fibers, in particular human hair, including in a cosmetic carrier at least one color-imparting compound and at least one tapioca starch, modified by means of propylene oxide, that has an average molecular weight (weight-average) from 700 to 1000 kDa, a propylene oxide content from 2.0 to 12.0 wt % (based on the weight of the tapioca starch modified by means of propylene oxide), and a viscosity from 3000 to 200,000 mPas (in 43-wt % aqueous solution, Brookfield viscometer, spindle 7, at 20° C. and 20 rpm).

R): A cosmetic agent for coloring keratinic fibers, in particular human hair, including in a cosmetic carrier at least one color-imparting compound and at least one tapioca starch, modified by means of propylene oxide, that has an average molecular weight (weight-average) from 700 to 1000 kDa, a propylene oxide content from 2.0 to 12.0 wt % (based on the weight of the tapioca starch modified by means of propylene oxide), and a viscosity from 10,000 to 100,000 mPas (in 43-wt % aqueous solution, Brookfield viscometer, spindle 7, at 20° C. and 20 rpm).

The examples A) to R) of the cosmetic agent according to the present specification preferably include as a color-imparting compound at least one oxidation dye precursor of the developer component type and optionally additionally at least one coupler component.

The respective features of the agent according to the present specification that are identified as preferred, such as in particular the quantities of the said starch modified by means of propylene oxide that are used, of course apply mutatis mutandis in the context of the embodiments A) to R).

The starch, modified by means of propylene oxide, that is used according to the present specification, produces its effect especially in agents for oxidative coloring of keratinic fibers, in particular human hair. It has therefore proven to be preferred to use an agent according to the present specification for oxidative coloring of keratinic fibers that includes, in a cosmetic carrier:
   (i) preferably at least one oxidation dye precursor of the developer component type and optionally additionally at least one coupler component, as a color-imparting compound;
   (ii) at least one starch, modified by means of propylene oxide, that possesses an average molecular weight (weight-average) from 50 to 2500 kDa and a propylene oxide content from 0.1 to 20.0 wt % (based on the weight of the starch modified by means of propylene oxide; and
   (iii) at least one oxidizing agent.

The previously recited preferred features (see above) apply with regard to (i) and (ii).

It is particularly preferred according to the present specification to add to the examples A) to R) according to the present specification:
   at least one oxidation dye precursor of the developer component type and optionally additionally at least one coupler component; and
   at least one oxidizing agent.

The oxidizing agents for purposes of the present specification are different from atmospheric oxygen and possess an oxidation potential enabling it to oxidize an oxidation dye precursor of the developer type. Relevant oxidizing agents are preferably hydrogen peroxide and/or at least one addition product thereof, in particular with inorganic or organic compounds, for example sodium perborate, sodium percarbonate, magnesium percarbonate, sodium percarbamide, polyvinylpyrrolidone.n $H_2O_2$ (n is a positive integer greater than 0), urea peroxide, and melamine peroxide.

The oxidizing agent is included in the cosmetic agent preferably in a quantity from 1.0 to 10.0 wt %, in particular from 3.0 to 10.0 wt %, based in each case on the weight of the ready-to-use cosmetic coloring agent.

In a preferred example of the present specification, the cosmetic coloring agent according to the present specification is mixed, prior to application, from a first composition including in a cosmetic carrier at least one color-changing component, and a second composition including in a cosmetic carrier at least one oxidizing agent, with the provision that the first composition or/and the second composition include at least one said starch modified by means of propylene oxide. The first and second composition are packaged separately from one another each in one compartment, and are furnished together in one packaging unit (kit). The two components are mixed with one another shortly before use. The resulting ready-to-use coloring preparation preferably has a pH in the range from 6.0 to 12.0, in particular from 7.5 to 10.0.

The cosmetic coloring agent according to the present specification preferably includes at least one alkalizing agent. The alkalizing agents usable according to the present specification are preferably selected from at least one representative of the group that is constituted from ammonia, basic amino acids, alkali hydroxides, alkanolamines, alkali metal metasilicates, urea, alkali phosphates, and alkali hydrogen phosphates. Lithium, sodium, potassium preferably serve as alkali metal ions, in particular sodium or potassium. It is preferred in turn if the alkalizing agents are different from ammonia.

The basic amino acids usable as alkalizing agents according to the present specification are preferably selected from the group that is constituted from L-arginine, D-arginine, D,L-arginine, L-histidine, D-histidine, D,L-histidine, L-lysine, D-lysine, D,L-lysine, particularly preferably L-arginine, D-arginine, D,L-arginine used as an alkalizing agent for purposes of the present specification.

The alkali hydroxides usable as an alkalizing agent according to the present specification are preferably selected from the group that is constituted from sodium hydroxide and potassium hydroxide.

The alkanolamines usable as an alkalizing agent according to the present specification are preferably selected from primary amines having a $C_2$ to $C_6$ alkyl basic structure that carries at least one hydroxyl group. Particularly preferred alkanolamines are selected from the group that is constituted from 2-aminoethan-1-ol (monoethanolamine), 3-aminopropan-1-ol, 4-aminobutan-1-ol, 5-aminopentan-1-ol, 1-aminopropan-2-ol, 1-aminobutan-2-ol, 1-aminopentan-2-ol, 1-aminopentan-3-ol, 1-aminopentan-4-ol, 3-amino-2-methylpropan-1-ol, 1-amino-2-methylpropan-2-ol, 3-aminopropane-1,2-diol, 2-amino-2-methylpropane-1,3-diol. Alkanolamines very particularly preferred according to the present specification are selected from the group of: 2-aminoethan-1-ol, 2-amino-2-methylpropan-1-ol, and 2-amino-2-methylpropane-1,3-diol.

The alkalizing agent is selected particularly preferably from at least one compound of the group that is constituted from 2-aminoethanol, 2-amino-2-methylpropan-1-ol, 2-amino-2-methylpropane-1,3-diol, potassium hydroxide, L-arginine, D-arginine, DL-arginine, N-methylglucamine, and urea.

The coloring agents according to the present specification can moreover include further active agents, adjuvants, and additives, for example nonionic polymers; cationic polymers; zwitterionic and amphoteric polymers; anionic polymers such as polyacrylic acids, crosslinked polyacrylic acids, vinyl acetate/crotonic acid copolymers, vinylpyrrolidone/vinyl acrylate copolymers, vinyl acetate/butyl maleate/isobornyl acrylate copolymers, methyl vinyl ether/maleic acid anhydride copolymers, and acrylic acid/ethyl acrylate/N-tert-butylacrylamide terpolymers; hair-conditioning compounds such as phospholipids; protein hydrolysates, in particular hydrolysates of elastin, collagen, keratin, milk, soy, and wheat protein, condensation products thereof with fatty acids, and quaternized protein hydrolysates; perfume oils, dimethylisosorbide, and cyclodextrins; fiber-structure-improving active agents, in particular mono-, di- and oligosaccharides such as glucose, galactose, fructose, fruit sugars, and lactose; cationic surfactants; defoamers; anti-dandruff active substances; light protection agents, in particular derivatized benzophenones, cinnamic acid derivatives, and triazines; active agents such as allantoin, pyrrolidonecarboxylic acids and salts thereof, as well as bisabolol; vitamins, provitamins, and vitamin precursors, in particular those of groups A, $B_3$, $B_5$, $B_6$, C, E, F, and H; plant extracts, in particular the extracts from green tea, oak bark, stinging nettle, witch hazel, hops, henna, chamomile, burdock, horsetail, whitethorn, linden blossom, almond, aloe vera, pine needles, horse chestnut, sandalwood, juniper, coconut, mango, apricot, lemon, wheat, kiwi, melon, orange, grapefruit, sage, rosemary, birch, mallow, lady's smock, wild thyme, yarrow, thyme, melissa, restharrow, coltsfoot, hibiscus, meristem, ginseng, or ginger root; cholesterol; consistency agents; fats and waxes; complexing agents; swelling and penetration substances; opacifiers; luster agents; solid pigments; stabilizing agents for hydrogen peroxide and other oxidizing agents; propellants; antioxidants.

The preferred embodiments of the first subject of the specification apply mutatis mutandis regarding the second subject of the specification.

A third subject of the present specification is a cosmetic method in which at least one starch, modified by means of propylene oxide, that possesses an average molecular weight (weight-average) from 50 to 2500 kDa and a propylene oxide content from 0.1 to 20.0 wt % (based on the weight of the starch modified by means of propylene oxide), acts on keratinic fibers (in particular human hair) artificially colored with at least one color-imparting compound and is rinsed off again after a contact time. A preferred example of this method according to the present specification is a method for coloring keratinic fibers in which an agent of the second subject of the present specification is applied onto the fibers and rinsed off again after a contact time.

The utilization temperatures can be in a range between 15 and 40° C. After a contact time as a rule from 5 to 45 minutes, the hair coloring agent is removed from the hair to be colored by being rinsed out. Subsequent washing with a shampoo is omitted if a carrier having a high surfactant content, e.g. a coloring shampoo, was used.

The preferred examples of the first and second subject of the specification apply mutatis mutandis regarding the third subject of the specification.

EXAMPLES 1.0 wt % (based on the total weight of the mixture) of a tapioca starch, modified with 5.5 wt % propylene oxide, having an average molecular weight ($M_w$) between 700 and 900 kDa and a viscosity of 55,000 mPas (43-wt % aqueous solution) was incorporated into the coloring cream of the commercial product IGORA ROYAL® 6-88 color cream. The resulting modified color cream was mixed, immediately before application onto hair strands (1 g "European natural hair 6/0" standardized hair, batch #06/2010, N93 of Kerling International, Germany, bonded at one end to produce a hair bundle), with a commercially usual 6-wt % hydrogen-peroxide-containing OXIGENTA® at a weight ratio of 1 to 1 to produce a hair coloring agent according to the present specification.

The ready-to-use coloring agent was then applied onto a hair strand at a weight ratio of 4 grams (g) coloring agent to 1 g hair, allowed to act for 30 minutes at 32° C., and rinsed off the fibers. A total of four hair strands were colored therewith. In addition, four hair strands were colored according to the above procedure using the above commercial product without addition of the aforesaid tapioca starch (not according to the specification).

The strands were each allowed to dry and were measured colorimetrically, determining the initial L, a, b values of each strand (Spectraflash 450 unit, Colortools software). Eight measurement points were taken for each hair strand, and for each value of the strands colored according to the present specification in one group, and the strands colored not according to the present specification in another group, the respective arithmetic mean of the group was determined, yielding the respective $L_0$, $a_0$, $b_0$ values. The same procedure was used for the subsequent colorimetric measurements.

In order to ascertain washing fastness, the hair strands were subjected to a washing procedure that simulates hair washing. More specifically, an ultrasonic bath was filled with aqueous shampoo solution (2 wt % "7 Kräuter" foaming shampoo).

The colored hair strands were immersed into this washing solution and treated therein with ultrasound (level 5) for 15 minutes. This treatment corresponds to the cleaning performance of six hair washes. The strands were then thoroughly rinsed, dried, and measured colorimetrically again. The strands were then subjected to a further washing cycle. The washing fastness was evaluated by calculating the color distance of the strands before washing and after each washing cycle, and is ascertained as follows using Formula (3).

$$\Delta E = [(L_i - L_0)^2 + (a_1 - a_0)^2 + (b_i - b_0)^2]^{1/2} \quad \text{Formula (3).}$$

In formula (3), $L_i$, $a_i$, $b_i$ are values after 6, 12, 18, 24, or 36 hair washes and $L_0$, $a_0$, $b_0$ are values after zero hair washes of hair strands. The change in color is indicated in Table (3) as a value $\Delta E$ after 6, 12, 18, 24, and 30 washes.

TABLE (1)

|  | No. of washes | | | | |
| --- | --- | --- | --- | --- | --- |
|  | 6 | 12 | 18 | 24 | 36 |
| Commercial product | 2.4 | 3.6 | 4.5 | 5.7 | 6.8 |
| Agent according to the present specification | 2.2 | 3.1 | 3.3 | 3.7 | 4.4 |

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention, it being understood that various changes may be made in the function and arrangement of elements described in an exemplary embodiment without departing from the scope of the invention as set forth in the appended claims and their legal equivalents.

What is claimed is:

1. A cosmetic agent for coloring keratinic fibers, comprising, in a cosmetic carrier:
    at least one color-imparting compound, in which the color-imparting compound comprises at least one of:
        an oxidation dye precursor of a developer component type; and
        a precursor of a bioanalogous dye; and
    at least one modified starch, the modified starch:
        being uncrosslinked;
        being modified by propylene oxide;
        having an average molecular weight between 50 and 2500 kiloDaltons (kDa); and
        having a propylene oxide content between 0.1 and 20.0 weight percent (wt %) based on the weight of the modified starch.

2. The cosmetic agent of claim 1, further comprising at least one oxidizing agent, the oxidizing agent comprising at least one of hydrogen peroxide and at least one addition product thereof.

3. The cosmetic agent of claim 1, in which the modified starch forms between 0.01 wt % and 40.0 wt % of the agent.

4. The cosmetic agent of claim 1, in which the modified starch forms between 0.5 wt % and 10.0 wt % of the agent.

5. The cosmetic agent of claim 1, in which the modified starch forms between 2.0 wt % and 6.0 wt % of the agent.

6. The cosmetic agent of claim 1, in which the color-imparting compound comprises at least one oxidation dye precursor of a developer component type.

7. The cosmetic agent of claim 1, in which the modified starch has an average molecular weight between 100 and 2000 kDa.

8. The cosmetic agent of claim 1, in which the modified starch has an average molecular weight between 500 and 1800 kDa.

9. The cosmetic agent of claim 1, in which the modified starch has an average molecular weight between 700 and 1000 kDa.

10. The cosmetic agent of claim 1, in which the modified starch has, in a 43-wt % solution in water, a viscosity between 150 and 1,500,000 millipascal seconds (mPa·s).

11. The cosmetic agent of claim 1, in which the modified starch has, in a 43-wt % solution in water, a viscosity between 3,000 and 200,000 millipascal seconds (mPa·s).

12. The cosmetic agent of claim 1, in which the modified starch has, in a 43-wt % solution in water, a viscosity between 10,000 and 100,000 millipascal seconds (mPa·s).

13. The cosmetic agent of claim 1, in which the modified starch has, in a 43-wt % solution in water, a viscosity between 40,000 and 70,000 millipascal seconds (mPa·s).

14. The cosmetic agent of claim 1, in which the modified starch is a tapioca starch modified by propylene oxide, a potato starch modified by propylene oxide, a corn starch modified by propylene oxide, or combinations thereof.

15. A method for providing a color treatment to keratinic fibers, the method comprising:
    applying at least one modified starch to keratinic fibers artificially colored with at least one color-imparting compound, in which:
        the at least one modified starch:
            is uncrosslinked;
            is modified by propylene oxide;
            has an average molecular weight between 50 and 2500 kiloDaltons (kDa); and
            has a propylene oxide content between 0.1 to 20 wt % based on the weight of the modified starch; and
        the color-imparting compound comprises at least one of:
            an oxidation dye precursor of a developer component type; and
            a precursor of a bioanalogous dye; and
    rinsing the at least one modified starch off the keratinic fibers after a contact time.

16. The method of claim 15, in which the at least one modified starch is applied to the keratinic fibers together with at least one color-imparting compound.

17. A method for using at least one modified starch to improve artificial color results of at least one color-imparting compound on hair, the method comprising:
    applying the at least one modified starch to hair, the at least one modified starch:
        being uncrosslinked;
        being modified by propylene oxide;
        having an average molecular weight between 50 and 2500 kiloDaltons (kDa); and
        having a propylene oxide content between 0.1 to 20.0 wt % based on the weight of the modified starch; and
    rinsing the modified starch from the hair;
    in which the color-imparting compound comprises at least one of:
        an oxidation dye precursor of a developer component type; and
        a precursor of a bioanalogous dye.

18. The cosmetic agent of claim 6, in which the color-imparting compound further comprises at least one coupler component.

19. The cosmetic agent of claim 18, in which the color-imparting compound includes an oxidation dye precursor comprising at least one of:
    at least one heterocyclic developer selected from pyrazole derivatives and pyrimidine derivatives and at least one compound selected from m-aminophenol or derivatives thereof as a coupler;
    4-amino-3-methylphenol, 5-amino-2-methylphenol;
    p-toluylenediamine, 4-amino-3-methylphenol, 5-amino-2-methylphenol; and
    2-(β-hydroxyethyl)-p-phenylenediamine, 4-amino-3-methylphenol, 5-amino-2-methylphenol.

* * * * *